(12) United States Patent
Messenger et al.

(10) Patent No.: US 9,646,481 B2
(45) Date of Patent: May 9, 2017

(54) ALARM SETTING AND INTERFACING WITH GESTURE CONTACT INTERFACING CONTROLS

(71) Applicant: FitBit, Inc., San Francisco, CA (US)

(72) Inventors: Jayson Messenger, San Francisco, CA (US); Shelten Yuen, Berkeley, CA (US)

(73) Assignee: FITBIT, INC., San Francisco, CA (US)

( * ) Notice: Subject to any disclaimer, the term of this patent is extended or adjusted under 35 U.S.C. 154(b) by 112 days.

(21) Appl. No.: 14/579,982

(22) Filed: Dec. 22, 2014

(65) Prior Publication Data

US 2015/0102923 A1 Apr. 16, 2015

Related U.S. Application Data

(63) Continuation of application No. 14/329,735, filed on Jul. 11, 2014, now Pat. No. 8,954,291, which is a (Continued)

(51) Int. Cl.
*G06F 19/00* (2011.01)
*G08B 25/00* (2006.01)
(Continued)

(52) U.S. Cl.
CPC .......... *G08B 25/008* (2013.01); *A61B 5/0022* (2013.01); *A61B 5/1118* (2013.01);
(Continued)

(58) Field of Classification Search
CPC ........ A61B 5/14532; A61B 2562/0295; A61B 5/7275
(Continued)

(56) References Cited

U.S. PATENT DOCUMENTS 2,717,736 A 9/1955 Schlesinger
2,827,309 A 3/1958 Fred
(Continued)

FOREIGN PATENT DOCUMENTS

CN 101978374 2/2011
CN 102111434 A 6/2011
(Continued)

OTHER PUBLICATIONS

Chandrasekar et al., "Plug-and-Play, Single-Chip Photoplethysmography", 34th Annual International Conference of the IEEE EMBS, San Diego, California USA, Aug. 28-Sep. 1, 2012, 4 pages.
(Continued)

*Primary Examiner* — Edward Raymond
(74) *Attorney, Agent, or Firm* — Knobbe Martens Olson & Bear LLP

(57) ABSTRACT

A device configured for capture of activity data for a user includes a housing, a sensor, a motor, a memory, and a processor. The sensor is disposed in the housing to track activity data of the user. The motor causes vibration of the housing. The memory stores an alarm setting that defines a time of day for triggering an alarm on the device. The processor activates the alarm upon reaching the time of day defined by the alarm setting, with the alarm causing the motor to produce the vibration of the housing. The sensor, which is interfaced with the processor, is configured to detect a current level of activity of the user. The processor is configured to automatically deactivate the alarm if the current level of activity qualifies for deactivating the alarm. The deactivating of the alarm causes the vibration of the device to be suspended.

24 Claims, 10 Drawing Sheets

Related U.S. Application Data continuation of application No. 14/050,305, filed on Oct. 9, 2013, now Pat. No. 8,812,259.

(60) Provisional application No. 61/886,000, filed on Oct. 2, 2013.

(51) Int. Cl.
| | |
|---|---|
| A61B 5/00 | (2006.01) |
| A61B 5/0205 | (2006.01) |
| A61B 5/021 | (2006.01) |
| A61B 5/024 | (2006.01) |
| A61B 5/11 | (2006.01) |
| A61B 5/22 | (2006.01) |
| G01C 22/00 | (2006.01) |

(52) U.S. Cl.
CPC .............. A61B 5/021 (2013.01); A61B 5/024 (2013.01); A61B 5/02055 (2013.01); A61B 5/1112 (2013.01); A61B 5/222 (2013.01); A61B 5/4809 (2013.01); A61B 5/4812 (2013.01); A61B 5/4815 (2013.01); A61B 5/6838 (2013.01); A61B 5/7264 (2013.01); A61B 2560/0214 (2013.01); A61B 2560/0242 (2013.01); A61B 2562/0219 (2013.01); G01C 22/006 (2013.01); G06F 19/3418 (2013.01); G06F 19/3481 (2013.01)

(58) Field of Classification Search
USPC .................. 702/160, 155, 182–185, 188
See application file for complete search history.

(56) References Cited

U.S. PATENT DOCUMENTS

| | | |
|---|---|---|
| 2,883,255 A | 4/1959 | Anderson |
| 3,163,856 A | 12/1964 | Kirby |
| 3,250,270 A | 5/1966 | Walter |
| 3,522,383 A | 7/1970 | Chang |
| 3,918,658 A | 11/1975 | Beller |
| 4,192,000 A | 3/1980 | Lipsey |
| 4,244,020 A | 1/1981 | Ratcliff |
| 4,281,663 A | 8/1981 | Pringle |
| 4,284,849 A | 8/1981 | Anderson et al. |
| 4,312,358 A | 1/1982 | Barney |
| 4,367,752 A | 1/1983 | Jimenez et al. |
| 4,390,922 A | 6/1983 | Pelliccia |
| 4,407,295 A | 10/1983 | Steuer et al. |
| 4,425,921 A | 1/1984 | Fujisaki et al. |
| 4,466,204 A | 8/1984 | Wu |
| 4,575,804 A | 3/1986 | Ratcliff |
| 4,578,769 A | 3/1986 | Frederick |
| 4,617,525 A | 10/1986 | Lloyd |
| 4,887,249 A | 12/1989 | Thinesen |
| 4,930,518 A | 6/1990 | Hrushesky |
| 4,977,509 A | 12/1990 | Pitchford et al. |
| 5,058,427 A | 10/1991 | Brandt |
| 5,224,059 A | 6/1993 | Nitta et al. |
| 5,295,085 A | 3/1994 | Hoffacker |
| 5,314,389 A | 5/1994 | Dotan |
| 5,323,650 A | 6/1994 | Fullen et al. |
| 5,365,930 A | 11/1994 | Takashima et al. |
| 5,446,705 A | 8/1995 | Haas et al. |
| 5,456,648 A | 10/1995 | Edinburg et al. |
| 5,553,296 A | 9/1996 | Forrest et al. |
| 5,583,776 A | 12/1996 | Levi et al. |
| 5,645,509 A | 7/1997 | Brewer et al. |
| 5,671,162 A | 9/1997 | Werbin |
| 5,692,324 A | 12/1997 | Goldston et al. |
| 5,704,350 A | 1/1998 | Williams, III |
| 5,724,265 A | 3/1998 | Hutchings |
| 5,817,008 A | 10/1998 | Rafert et al. |
| 5,890,128 A | 3/1999 | Diaz et al. |
| 5,891,042 A | 4/1999 | Sham et al. |
| 5,894,454 A | 4/1999 | Kondo |
| 5,899,963 A | 5/1999 | Hutchings |
| 5,941,828 A | 8/1999 | Archibald et al. |
| 5,947,868 A | 9/1999 | Dugan |
| 5,955,667 A | 9/1999 | Fyfe |
| 5,976,083 A | 11/1999 | Richardson et al. |
| 6,018,705 A | 1/2000 | Gaudet et al. |
| 6,077,193 A | 6/2000 | Buhler et al. |
| 6,078,874 A | 6/2000 | Piety et al. |
| 6,085,248 A | 7/2000 | Sambamurthy et al. |
| 6,129,686 A | 10/2000 | Friedman |
| 6,145,389 A | 11/2000 | Ebeling et al. |
| 6,183,425 B1 | 2/2001 | Whalen et al. |
| 6,213,872 B1 | 4/2001 | Harada et al. |
| 6,241,684 B1 | 6/2001 | Amano et al. |
| 6,287,262 B1 | 9/2001 | Amano et al. |
| 6,301,964 B1 | 10/2001 | Fyfe et al. |
| 6,302,789 B2 | 10/2001 | Harada et al. |
| 6,305,221 B1 | 10/2001 | Hutchings |
| 6,309,360 B1 | 10/2001 | Mault |
| 6,454,708 B1 | 9/2002 | Ferguson et al. |
| 6,469,639 B2 | 10/2002 | Tanenhaus et al. |
| 6,478,736 B1 | 11/2002 | Mault |
| 6,513,381 B2 | 2/2003 | Fyfe et al. |
| 6,513,532 B2 | 2/2003 | Mault et al. |
| 6,527,711 B1 | 3/2003 | Stivoric et al. |
| 6,529,827 B1 | 3/2003 | Beason et al. |
| 6,558,335 B1 | 5/2003 | Thede |
| 6,561,951 B2 | 5/2003 | Cannon et al. |
| 6,571,200 B1 | 5/2003 | Mault |
| 6,583,369 B2 | 6/2003 | Montagnino et al. |
| 6,585,622 B1 | 7/2003 | Shum et al. |
| 6,607,493 B2 | 8/2003 | Song |
| 6,620,078 B2 | 9/2003 | Pfeffer |
| 6,678,629 B2 | 1/2004 | Tsuji |
| 6,699,188 B2 | 3/2004 | Wessel |
| 6,761,064 B2 | 7/2004 | Tsuji |
| 6,772,331 B1 | 8/2004 | Hind et al. |
| 6,788,200 B1 | 9/2004 | Jamel et al. |
| 6,790,178 B1 | 9/2004 | Mault et al. |
| 6,808,473 B2 | 10/2004 | Hisano et al. |
| 6,811,516 B1 | 11/2004 | Dugan |
| 6,813,582 B2 | 11/2004 | Levi et al. |
| 6,813,931 B2 | 11/2004 | Yadav et al. |
| 6,856,938 B2 | 2/2005 | Kurtz |
| 6,862,575 B1 | 3/2005 | Anttila et al. |
| 6,984,207 B1 | 1/2006 | Sullivan et al. |
| 7,020,508 B2 | 3/2006 | Stivoric et al. |
| 7,041,032 B1 | 5/2006 | Calvano |
| 7,062,225 B2 | 6/2006 | White |
| 7,099,237 B2 | 8/2006 | Lall |
| 7,133,690 B2 | 11/2006 | Ranta-Aho et al. |
| 7,162,368 B2 | 1/2007 | Levi et al. |
| 7,171,331 B2 | 1/2007 | Vock et al. |
| 7,200,517 B2 | 4/2007 | Darley et al. |
| 7,246,033 B1 | 7/2007 | Kudo |
| 7,261,690 B2 | 8/2007 | Teller et al. |
| 7,272,982 B2 | 9/2007 | Neuhauser et al. |
| 7,283,870 B2 | 10/2007 | Kaiser et al. |
| 7,285,090 B2 | 10/2007 | Stivoric et al. |
| 7,373,820 B1 | 5/2008 | James |
| 7,443,292 B2 | 10/2008 | Jensen et al. |
| 7,457,724 B2 | 11/2008 | Vock et al. |
| 7,467,060 B2 | 12/2008 | Kulach et al. |
| 7,502,643 B2 | 3/2009 | Farringdon et al. |
| 7,505,865 B2 | 3/2009 | Ohkubo et al. |
| 7,539,532 B2 | 5/2009 | Tran |
| 7,558,622 B2 | 7/2009 | Tran |
| 7,559,877 B2 | 7/2009 | Parks et al. |
| 7,608,050 B2 | 10/2009 | Shugg |
| 7,653,508 B1 | 1/2010 | Kahn et al. |
| 7,690,556 B1 | 4/2010 | Kahn et al. |
| 7,713,173 B2 | 5/2010 | Shin et al. |
| 7,762,952 B2 | 7/2010 | Lee et al. |
| 7,771,320 B2 | 8/2010 | Riley et al. |
| 7,774,156 B2 | 8/2010 | Niva et al. |
| 7,789,802 B2 | 9/2010 | Lee et al. |
| 7,827,000 B2 | 11/2010 | Stirling et al. |
| 7,865,140 B2 | 1/2011 | Levien et al. |

(56) References Cited

U.S. PATENT DOCUMENTS

| | | |
|---|---|---|
| 7,881,902 B1 | 2/2011 | Kahn et al. |
| 7,907,901 B1 | 3/2011 | Kahn et al. |
| 7,925,022 B2 | 4/2011 | Jung et al. |
| 7,927,253 B2 | 4/2011 | Vincent et al. |
| 7,941,665 B2 | 5/2011 | Berkema et al. |
| 7,942,824 B1 | 5/2011 | Kayyali et al. |
| 7,953,549 B2 | 5/2011 | Graham et al. |
| 7,983,876 B2 | 7/2011 | Vock et al. |
| 8,005,922 B2 | 8/2011 | Boudreau et al. |
| 8,028,443 B2 | 10/2011 | Case, Jr. |
| 8,036,850 B2 | 10/2011 | Kulach et al. |
| 8,055,469 B2 | 11/2011 | Kulach et al. |
| 8,059,573 B2 | 11/2011 | Julian et al. |
| 8,060,337 B2 | 11/2011 | Kulach et al. |
| 8,095,071 B2 | 1/2012 | Sim et al. |
| 8,099,318 B2 | 1/2012 | Moukas et al. |
| 8,103,247 B2 | 1/2012 | Ananthanarayanan et al. |
| 8,132,037 B2 | 3/2012 | Fehr et al. |
| 8,172,761 B1 | 5/2012 | Rulkov et al. |
| 8,177,260 B2 | 5/2012 | Tropper et al. |
| 8,180,591 B2 | 5/2012 | Yuen et al. |
| 8,180,592 B2 | 5/2012 | Yuen et al. |
| 8,190,651 B2 | 5/2012 | Treu et al. |
| 8,213,613 B2 | 7/2012 | Diehl et al. |
| 8,260,261 B2 | 9/2012 | Teague |
| 8,270,297 B2 | 9/2012 | Akasaka et al. |
| 8,271,662 B1 | 9/2012 | Gossweiler, III et al. |
| 8,289,162 B2 | 10/2012 | Mooring et al. |
| 8,311,769 B2 | 11/2012 | Yuen et al. |
| 8,311,770 B2 | 11/2012 | Yuen et al. |
| 8,386,008 B2 | 2/2013 | Yuen et al. |
| 8,437,980 B2 | 5/2013 | Yuen et al. |
| 8,462,591 B1 | 6/2013 | Marhaben |
| 8,463,576 B2 | 6/2013 | Yuen et al. |
| 8,463,577 B2 | 6/2013 | Yuen et al. |
| 8,487,771 B2 | 7/2013 | Hsieh et al. |
| 8,533,269 B2 | 9/2013 | Brown |
| 8,533,620 B2 | 9/2013 | Hoffman et al. |
| 8,543,185 B2 | 9/2013 | Yuen et al. |
| 8,543,351 B2 | 9/2013 | Yuen et al. |
| 8,548,770 B2 | 10/2013 | Yuen et al. |
| 8,562,489 B2 | 10/2013 | Burton et al. |
| 8,583,402 B2 | 11/2013 | Yuen et al. |
| 8,597,093 B2 | 12/2013 | Engelberg et al. |
| 8,634,796 B2 | 1/2014 | Johnson |
| 8,638,228 B2 | 1/2014 | Amigo et al. |
| 8,670,953 B2 | 3/2014 | Yuen et al. |
| 8,684,900 B2 | 4/2014 | Tran |
| 8,690,578 B1 | 4/2014 | Nusbaum et al. |
| 8,738,321 B2 | 5/2014 | Yuen et al. |
| 8,738,323 B2 | 5/2014 | Yuen et al. |
| 8,744,803 B2 | 6/2014 | Park et al. |
| 8,762,101 B2 | 6/2014 | Yuen et al. |
| 8,764,651 B2 | 7/2014 | Tran |
| 8,825,445 B2 | 9/2014 | Hoffman et al. |
| 8,847,988 B2 | 9/2014 | Geisner et al. |
| 8,868,377 B2 | 10/2014 | Yuen et al. |
| 8,892,401 B2 | 11/2014 | Yuen et al. |
| 8,949,070 B1 | 2/2015 | Kahn et al. |
| 8,954,290 B2 | 2/2015 | Yuen et al. |
| 8,961,414 B2 | 2/2015 | Teller et al. |
| 8,968,195 B2 | 3/2015 | Tran |
| 9,047,648 B1 | 6/2015 | Lekutai et al. |
| 9,081,534 B2 | 7/2015 | Yuen et al. |
| 9,374,279 B2 | 6/2016 | Yuen et al. |
| 9,426,769 B2 | 8/2016 | Haro |
| 2001/0049470 A1 | 12/2001 | Mault et al. |
| 2001/0055242 A1 | 12/2001 | Deshmukh et al. |
| 2002/0013717 A1 | 1/2002 | Ando et al. |
| 2002/0019585 A1 | 2/2002 | Dickenson |
| 2002/0077219 A1 | 6/2002 | Cohen et al. |
| 2002/0082144 A1 | 6/2002 | Pfeffer |
| 2002/0087264 A1 | 7/2002 | Hills et al. |
| 2002/0109600 A1 | 8/2002 | Mault et al. |
| 2002/0178060 A1 | 11/2002 | Sheehan |
| 2002/0191797 A1 | 12/2002 | Perlman |
| 2002/0198776 A1 | 12/2002 | Nara et al. |
| 2003/0018523 A1 | 1/2003 | Rappaport et al. |
| 2003/0050537 A1 | 3/2003 | Wessel |
| 2003/0065561 A1 | 4/2003 | Brown et al. |
| 2003/0107575 A1 | 6/2003 | Cardno |
| 2003/0131059 A1 | 7/2003 | Brown et al. |
| 2003/0171189 A1 | 9/2003 | Kaufman |
| 2003/0208335 A1 | 11/2003 | Unuma et al. |
| 2003/0226695 A1 | 12/2003 | Mault |
| 2004/0054497 A1 | 3/2004 | Kurtz |
| 2004/0061324 A1 | 4/2004 | Howard |
| 2004/0117963 A1 | 6/2004 | Schneider |
| 2004/0122488 A1 | 6/2004 | Mazar et al. |
| 2004/0152957 A1 | 8/2004 | Stivoric et al. |
| 2004/0239497 A1 | 12/2004 | Schwartzman et al. |
| 2004/0249299 A1 | 12/2004 | Cobb |
| 2004/0257557 A1 | 12/2004 | Block |
| 2005/0037844 A1 | 2/2005 | Shum et al. |
| 2005/0038679 A1 | 2/2005 | Short |
| 2005/0054938 A1 | 3/2005 | Wehman et al. |
| 2005/0102172 A1 | 5/2005 | Sirmans, Jr. |
| 2005/0107723 A1 | 5/2005 | Wehman et al. |
| 2005/0163056 A1 | 7/2005 | Ranta-Aho et al. |
| 2005/0171410 A1 | 8/2005 | Hjelt et al. |
| 2005/0186965 A1 | 8/2005 | Pagonis et al. |
| 2005/0187481 A1 | 8/2005 | Hatib |
| 2005/0195830 A1 | 9/2005 | Chitrapu et al. |
| 2005/0216724 A1 | 9/2005 | Isozaki |
| 2005/0228244 A1 | 10/2005 | Banet |
| 2005/0228692 A1 | 10/2005 | Hodgdon |
| 2005/0234742 A1 | 10/2005 | Hodgdon |
| 2005/0248718 A1 | 11/2005 | Howell et al. |
| 2005/0272564 A1 | 12/2005 | Pyles et al. |
| 2006/0004265 A1 | 1/2006 | Pulkkinen et al. |
| 2006/0020174 A1 | 1/2006 | Matsumura |
| 2006/0020177 A1 | 1/2006 | Seo et al. |
| 2006/0025282 A1 | 2/2006 | Redmann |
| 2006/0039348 A1 | 2/2006 | Racz et al. |
| 2006/0047208 A1 | 3/2006 | Yoon |
| 2006/0047447 A1 | 3/2006 | Brady et al. |
| 2006/0064037 A1 | 3/2006 | Shalon et al. |
| 2006/0064276 A1 | 3/2006 | Ren et al. |
| 2006/0069619 A1 | 3/2006 | Walker et al. |
| 2006/0089542 A1 | 4/2006 | Sands |
| 2006/0106535 A1 | 5/2006 | Duncan |
| 2006/0111944 A1 | 5/2006 | Sirmans, Jr. |
| 2006/0129436 A1 | 6/2006 | Short |
| 2006/0143645 A1 | 6/2006 | Vock et al. |
| 2006/0166718 A1 | 7/2006 | Seshadri et al. |
| 2006/0189863 A1 | 8/2006 | Peyser |
| 2006/0217231 A1 | 9/2006 | Parks et al. |
| 2006/0247952 A1 | 11/2006 | Muraca |
| 2006/0277474 A1 | 12/2006 | Robarts et al. |
| 2006/0282021 A1 | 12/2006 | DeVaul et al. |
| 2006/0287883 A1 | 12/2006 | Turgiss et al. |
| 2006/0288117 A1 | 12/2006 | Raveendran et al. |
| 2007/0011028 A1 | 1/2007 | Sweeney |
| 2007/0049384 A1 | 3/2007 | King et al. |
| 2007/0050715 A1 | 3/2007 | Behar |
| 2007/0051369 A1 | 3/2007 | Choi et al. |
| 2007/0061593 A1 | 3/2007 | Celikkan et al. |
| 2007/0071643 A1 | 3/2007 | Hall et al. |
| 2007/0072156 A1 | 3/2007 | Kaufman et al. |
| 2007/0083095 A1 | 4/2007 | Rippo et al. |
| 2007/0083602 A1 | 4/2007 | Heggenhougen et al. |
| 2007/0123391 A1 | 5/2007 | Shin et al. |
| 2007/0135264 A1 | 6/2007 | Rosenberg |
| 2007/0136093 A1 | 6/2007 | Rankin et al. |
| 2007/0146116 A1 | 6/2007 | Kimbrell |
| 2007/0155277 A1 | 7/2007 | Amitai et al. |
| 2007/0159926 A1 | 7/2007 | Prstojevich et al. |
| 2007/0179356 A1 | 8/2007 | Wessel |
| 2007/0179761 A1 | 8/2007 | Wren et al. |
| 2007/0194066 A1 | 8/2007 | Ishihara et al. |
| 2007/0197920 A1 | 8/2007 | Adams |
| 2007/0208544 A1 | 9/2007 | Kulach et al. |
| 2007/0276271 A1 | 11/2007 | Chan |
| 2007/0288265 A1 | 12/2007 | Quinian et al. |

(56) References Cited

U.S. PATENT DOCUMENTS

| | | |
|---|---|---|
| 2008/0001735 A1 | 1/2008 | Tran |
| 2008/0014947 A1 | 1/2008 | Carnall |
| 2008/0022089 A1 | 1/2008 | Leedom |
| 2008/0032864 A1 | 2/2008 | Hakki |
| 2008/0044014 A1 | 2/2008 | Corndorf |
| 2008/0054072 A1 | 3/2008 | Katragadda et al. |
| 2008/0084823 A1 | 4/2008 | Akasaka et al. |
| 2008/0093838 A1 | 4/2008 | Tropper et al. |
| 2008/0097550 A1 | 4/2008 | Dicks et al. |
| 2008/0109158 A1 | 5/2008 | Huhtala |
| 2008/0114829 A1 | 5/2008 | Button et al. |
| 2008/0125288 A1 | 5/2008 | Case |
| 2008/0125959 A1 | 5/2008 | Doherty |
| 2008/0129457 A1 | 6/2008 | Ritter et al. |
| 2008/0134102 A1 | 6/2008 | Movold et al. |
| 2008/0139910 A1 | 6/2008 | Mastrototaro et al. |
| 2008/0140163 A1 | 6/2008 | Keacher et al. |
| 2008/0140338 A1 | 6/2008 | No et al. |
| 2008/0146892 A1 | 6/2008 | LeBoeuf et al. |
| 2008/0155077 A1 | 6/2008 | James |
| 2008/0176655 A1 | 7/2008 | James et al. |
| 2008/0190202 A1 | 8/2008 | Kulach et al. |
| 2008/0214360 A1 | 9/2008 | Stirling et al. |
| 2008/0275309 A1 | 11/2008 | Stivoric et al. |
| 2008/0285805 A1 | 11/2008 | Luinge et al. |
| 2008/0287751 A1 | 11/2008 | Stivoric et al. |
| 2008/0300641 A1 | 12/2008 | Brunekreeft |
| 2009/0012418 A1 | 1/2009 | Gerlach |
| 2009/0018797 A1 | 1/2009 | Kasama et al. |
| 2009/0043531 A1 | 2/2009 | Kahn et al. |
| 2009/0047645 A1 | 2/2009 | Dibenedetto et al. |
| 2009/0048044 A1 | 2/2009 | Oleson et al. |
| 2009/0054737 A1 | 2/2009 | Magar et al. |
| 2009/0054751 A1 | 2/2009 | Babashan et al. |
| 2009/0058635 A1 | 3/2009 | LaLonde et al. |
| 2009/0063193 A1 | 3/2009 | Barton et al. |
| 2009/0063293 A1 | 3/2009 | Mirrashidi et al. |
| 2009/0076765 A1 | 3/2009 | Kulach et al. |
| 2009/0088183 A1 | 4/2009 | Piersol |
| 2009/0093341 A1 | 4/2009 | James et al. |
| 2009/0098821 A1 | 4/2009 | Shinya |
| 2009/0144456 A1 | 6/2009 | Gelf et al. |
| 2009/0144639 A1 | 6/2009 | Nims et al. |
| 2009/0150178 A1 | 6/2009 | Sutton et al. |
| 2009/0156172 A1 | 6/2009 | Chan |
| 2009/0171788 A1 | 7/2009 | Tropper et al. |
| 2009/0195350 A1 | 8/2009 | Tsern et al. |
| 2009/0262088 A1 | 10/2009 | Moll-Carrillo et al. |
| 2009/0264713 A1 | 10/2009 | Van Loenen et al. |
| 2009/0271147 A1 | 10/2009 | Sugai |
| 2009/0287921 A1 | 11/2009 | Zhu et al. |
| 2009/0307517 A1 | 12/2009 | Fehr et al. |
| 2009/0309742 A1 | 12/2009 | Alexander et al. |
| 2009/0313857 A1 | 12/2009 | Carnes et al. |
| 2010/0023348 A1 | 1/2010 | Hardee et al. |
| 2010/0043056 A1 | 2/2010 | Ganapathy |
| 2010/0058064 A1 | 3/2010 | Kirovski et al. |
| 2010/0059561 A1 | 3/2010 | Ellis et al. |
| 2010/0069203 A1 | 3/2010 | Kawaguchi et al. |
| 2010/0079291 A1 | 4/2010 | Kroll |
| 2010/0125729 A1 | 5/2010 | Baentsch et al. |
| 2010/0130873 A1 | 5/2010 | Yuen et al. |
| 2010/0158494 A1 | 6/2010 | King |
| 2010/0159709 A1 | 6/2010 | Kotani et al. |
| 2010/0167783 A1 | 7/2010 | Alameh et al. |
| 2010/0179411 A1 | 7/2010 | Holmström et al. |
| 2010/0185064 A1 | 7/2010 | Bandic et al. |
| 2010/0191153 A1 | 7/2010 | Sanders et al. |
| 2010/0205541 A1 | 8/2010 | Rapaport et al. |
| 2010/0217099 A1 | 8/2010 | LeBoeuf et al. |
| 2010/0222179 A1 | 9/2010 | Temple et al. |
| 2010/0261987 A1 | 10/2010 | Kamath et al. |
| 2010/0292050 A1 | 11/2010 | DiBenedetto |
| 2010/0292600 A1 | 11/2010 | DiBenedetto et al. |
| 2010/0295684 A1 | 11/2010 | Hsieh et al. |
| 2010/0298656 A1 | 11/2010 | McCombie et al. |
| 2010/0298661 A1 | 11/2010 | McCombie et al. |
| 2010/0304674 A1 | 12/2010 | Kim et al. |
| 2010/0311544 A1 | 12/2010 | Robinette et al. |
| 2010/0331145 A1 | 12/2010 | Lakovic et al. |
| 2011/0003665 A1 | 1/2011 | Burton et al. |
| 2011/0009051 A1 | 1/2011 | Khedouri et al. |
| 2011/0021143 A1 | 1/2011 | Kapur et al. |
| 2011/0022349 A1 | 1/2011 | Stirling et al. |
| 2011/0029241 A1 | 2/2011 | Miller et al. |
| 2011/0032105 A1 | 2/2011 | Hoffman et al. |
| 2011/0051665 A1 | 3/2011 | Huang |
| 2011/0080349 A1 | 4/2011 | Holbein et al. |
| 2011/0087076 A1 | 4/2011 | Brynelsen et al. |
| 2011/0106449 A1 | 5/2011 | Chowdhary et al. |
| 2011/0109540 A1 | 5/2011 | Milne et al. |
| 2011/0131005 A1 | 6/2011 | Ueshima et al. |
| 2011/0145894 A1 | 6/2011 | Garcia Morchon et al. |
| 2011/0153773 A1 | 6/2011 | Vandwalle |
| 2011/0167262 A1 | 7/2011 | Ross et al. |
| 2011/0193704 A1* | 8/2011 | Harper ............... A61B 5/14532 340/573.1 |
| 2011/0197157 A1 | 8/2011 | Hoffman et al. |
| 2011/0214030 A1 | 9/2011 | Greenberg et al. |
| 2011/0221590 A1 | 9/2011 | Baker et al. |
| 2011/0224508 A1 | 9/2011 | Moon |
| 2011/0230729 A1 | 9/2011 | Shirasaki et al. |
| 2011/0258689 A1 | 10/2011 | Cohen et al. |
| 2011/0275940 A1 | 11/2011 | Nims et al. |
| 2012/0015778 A1 | 1/2012 | Lee et al. |
| 2012/0035487 A1 | 2/2012 | Werner et al. |
| 2012/0046113 A1 | 2/2012 | Ballas |
| 2012/0072165 A1 | 3/2012 | Jallon |
| 2012/0083705 A1 | 4/2012 | Yuen et al. |
| 2012/0083714 A1 | 4/2012 | Yuen et al. |
| 2012/0083715 A1 | 4/2012 | Yuen et al. |
| 2012/0083716 A1 | 4/2012 | Yuen et al. |
| 2012/0084053 A1 | 4/2012 | Yuen et al. |
| 2012/0084054 A1 | 4/2012 | Yuen et al. |
| 2012/0092157 A1 | 4/2012 | Tran |
| 2012/0094649 A1 | 4/2012 | Porrati et al. |
| 2012/0102008 A1 | 4/2012 | Kääriäinen et al. |
| 2012/0116684 A1 | 5/2012 | Ingrassia, Jr. et al. |
| 2012/0119911 A1 | 5/2012 | Jeon et al. |
| 2012/0150483 A1 | 6/2012 | Vock et al. |
| 2012/0165684 A1 | 6/2012 | Sholder |
| 2012/0166257 A1 | 6/2012 | Shiragami et al. |
| 2012/0179278 A1 | 7/2012 | Riley et al. |
| 2012/0183939 A1 | 7/2012 | Aragones et al. |
| 2012/0215328 A1 | 8/2012 | Schmelzer |
| 2012/0221634 A1 | 8/2012 | Treu et al. |
| 2012/0226471 A1 | 9/2012 | Yuen et al. |
| 2012/0226472 A1 | 9/2012 | Yuen et al. |
| 2012/0227737 A1 | 9/2012 | Mastrototaro et al. |
| 2012/0245716 A1 | 9/2012 | Srinivasan et al. |
| 2012/0254987 A1 | 10/2012 | Ge et al. |
| 2012/0265477 A1 | 10/2012 | Vock et al. |
| 2012/0265480 A1 | 10/2012 | Oshima |
| 2012/0274508 A1 | 11/2012 | Brown et al. |
| 2012/0283855 A1 | 11/2012 | Hoffman et al. |
| 2012/0290109 A1 | 11/2012 | Engelberg et al. |
| 2012/0296400 A1 | 11/2012 | Bierman et al. |
| 2012/0297229 A1 | 11/2012 | Desai et al. |
| 2012/0297440 A1 | 11/2012 | Reams et al. |
| 2012/0316456 A1 | 12/2012 | Rahman et al. |
| 2012/0324226 A1 | 12/2012 | Bichsel et al. |
| 2012/0330109 A1 | 12/2012 | Tran |
| 2013/0006718 A1 | 1/2013 | Nielsen et al. |
| 2013/0041590 A1 | 2/2013 | Burich et al. |
| 2013/0072169 A1 | 3/2013 | Ross et al. |
| 2013/0073254 A1 | 3/2013 | Yuen et al. |
| 2013/0073255 A1 | 3/2013 | Yuen et al. |
| 2013/0080113 A1 | 3/2013 | Yuen et al. |
| 2013/0094600 A1 | 4/2013 | Beziat et al. |
| 2013/0095459 A1 | 4/2013 | Tran |
| 2013/0096843 A1 | 4/2013 | Yuen et al. |
| 2013/0102251 A1 | 4/2013 | Linde et al. |
| 2013/0103847 A1 | 4/2013 | Brown et al. |
| 2013/0106684 A1 | 5/2013 | Weast et al. |

(56) References Cited

U.S. PATENT DOCUMENTS

| | | |
|---|---|---|
| 2013/0132501 A1 | 5/2013 | Vandwalle et al. |
| 2013/0151193 A1 | 6/2013 | Kulach et al. |
| 2013/0151196 A1 | 6/2013 | Yuen et al. |
| 2013/0158369 A1 | 6/2013 | Yuen et al. |
| 2013/0166048 A1 | 6/2013 | Werner et al. |
| 2013/0187789 A1 | 7/2013 | Lowe |
| 2013/0190008 A1 | 7/2013 | Vathsangam et al. |
| 2013/0190903 A1 | 7/2013 | Balakrishnan et al. |
| 2013/0191034 A1 | 7/2013 | Weast et al. |
| 2013/0203475 A1 | 8/2013 | Kil et al. |
| 2013/0209972 A1 | 8/2013 | Carter et al. |
| 2013/0225117 A1 | 8/2013 | Giacoletto et al. |
| 2013/0228063 A1 | 9/2013 | Turner |
| 2013/0231574 A1 | 9/2013 | Tran |
| 2013/0238287 A1 | 9/2013 | Hoffman et al. |
| 2013/0261475 A1 | 10/2013 | Mochizuki |
| 2013/0267249 A1 | 10/2013 | Rosenberg |
| 2013/0268199 A1 | 10/2013 | Nielsen et al. |
| 2013/0268236 A1 | 10/2013 | Yuen et al. |
| 2013/0268687 A1 | 10/2013 | Schrecker |
| 2013/0268767 A1 | 10/2013 | Schrecker |
| 2013/0274904 A1 | 10/2013 | Coza et al. |
| 2013/0281110 A1 | 10/2013 | Zelinka |
| 2013/0289366 A1 | 10/2013 | Chua et al. |
| 2013/0296666 A1 | 11/2013 | Kumar et al. |
| 2013/0296672 A1 | 11/2013 | O'Neil et al. |
| 2013/0296673 A1 | 11/2013 | Thaveeprungsriporn et al. |
| 2013/0297220 A1 | 11/2013 | Yuen et al. |
| 2013/0310896 A1 | 11/2013 | Mass |
| 2013/0325396 A1 | 12/2013 | Yuen et al. |
| 2013/0331058 A1 | 12/2013 | Harvey |
| 2013/0337974 A1 | 12/2013 | Yanev et al. |
| 2013/0345978 A1 | 12/2013 | Lush et al. |
| 2014/0035761 A1 | 2/2014 | Burton et al. |
| 2014/0035764 A1 | 2/2014 | Burton et al. |
| 2014/0039804 A1 | 2/2014 | Park et al. |
| 2014/0039840 A1 | 2/2014 | Yuen et al. |
| 2014/0039841 A1 | 2/2014 | Yuen et al. |
| 2014/0052280 A1 | 2/2014 | Yuen et al. |
| 2014/0067278 A1 | 3/2014 | Yuen et al. |
| 2014/0077673 A1 | 3/2014 | Garg et al. |
| 2014/0085077 A1 | 3/2014 | Luna et al. |
| 2014/0094941 A1 | 4/2014 | Ellis et al. |
| 2014/0099614 A1 | 4/2014 | Hu et al. |
| 2014/0121471 A1 | 5/2014 | Walker |
| 2014/0125618 A1 | 5/2014 | Panther et al. |
| 2014/0156228 A1 | 6/2014 | Yuen et al. |
| 2014/0164611 A1 | 6/2014 | Molettiere et al. |
| 2014/0180022 A1 | 6/2014 | Stivoric et al. |
| 2014/0191866 A1 | 7/2014 | Yuen et al. |
| 2014/0200691 A1 | 7/2014 | Lee et al. |
| 2014/0207264 A1 | 7/2014 | Quy |
| 2014/0213858 A1 | 7/2014 | Presura et al. |
| 2014/0275885 A1 | 9/2014 | Isaacson et al. |
| 2014/0278229 A1 | 9/2014 | Hong et al. |
| 2014/0316305 A1 | 10/2014 | Venkatraman et al. |
| 2014/0337451 A1 | 11/2014 | Choudhary et al. |
| 2014/0337621 A1 | 11/2014 | Nakhimov |
| 2014/0343867 A1 | 11/2014 | Yuen et al. |
| 2015/0026647 A1 | 1/2015 | Park et al. |
| 2015/0057967 A1 | 2/2015 | Albinali |
| 2015/0088457 A1 | 3/2015 | Yuen et al. |
| 2015/0120186 A1 | 4/2015 | Heikes |
| 2015/0127268 A1 | 5/2015 | Park et al. |
| 2015/0137994 A1 | 5/2015 | Rahman et al. |
| 2015/0220883 A1 | 8/2015 | B'Far et al. |
| 2015/0289802 A1 | 10/2015 | Thomas et al. |
| 2015/0324541 A1 | 11/2015 | Cheung et al. |
| 2015/0374267 A1 | 12/2015 | Laughlin |
| 2016/0058372 A1 | 3/2016 | Raghuram et al. |
| 2016/0061626 A1 | 3/2016 | Burton et al. |
| 2016/0063888 A1 | 3/2016 | McCallum et al. |
| 2016/0089572 A1 | 3/2016 | Liu et al. |
| 2016/0107646 A1 | 4/2016 | Kolisetty et al. |
| 2016/0259426 A1 | 9/2016 | Yuen et al. |
| 2016/0278669 A1 | 9/2016 | Messenger et al. |
| 2016/0285985 A1 | 9/2016 | Molettiere et al. |
| 2016/0323401 A1 | 11/2016 | Messenger et al. |

FOREIGN PATENT DOCUMENTS

| | | |
|---|---|---|
| CN | 102377815 A | 3/2012 |
| CN | 102740933 | 10/2012 |
| CN | 102983890 | 3/2013 |
| CN | 103226647 | 7/2013 |
| EP | 1 721 237 | 11/2006 |
| JP | 11347021 A | 12/1999 |
| RU | 2178588 C1 | 1/2002 |
| WO | WO 0211019 | 2/2002 |
| WO | WO 2006055125 | 5/2006 |
| WO | WO 2006090197 | 8/2006 |
| WO | WO 2008038141 | 4/2008 |
| WO | WO 2009042965 | 4/2009 |
| WO | WO 2012061438 | 5/2012 |
| WO | WO 12/170586 | 12/2012 |
| WO | WO 12/170924 | 12/2012 |
| WO | WO 12/171032 | 12/2012 |
| WO | WO 15/127067 | 8/2015 |
| WO | WO 16/003269 | 1/2016 |

OTHER PUBLICATIONS

Clifford et al., "Altimeter and Barometer System", Freescale Semiconductor Application Note AN1979, Rev. 3, Nov. 2006, 10 pages.

Fang et al, "Design of a Wireless Assisted Pedestrian Dead Reckoning System—The NavMote Experience", IEEE Transactions on Instrumentation and Measurement, vol. 54, No. 6, Dec. 2005, pp. 2342-2358.

Fitbit Inc., "Fitbit Automatically Tracks Your Fitness and Sleep" published online at web.archive.org/web/20080910224820/http://www.fitbit.com, copyright Sep. 10, 2008, 1 page.

Godfrey et al., "Direct Measurement of Human Movement by Accelerometry", Medical Engineering & Physics, vol. 30, 2008, pp. 1364-1386 (22 pages).

Godha et al., "Foot Mounted Inertia System for Pedestrian Naviation", Measurement Science and Technology, vol. 19, No. 7, May 2008, pp. 1-9 (10 pages).

Intersema, "Using MS5534 for altimeters and barometers", Application Note AN501, Jan. 2006, 12pages.

Ladetto et al, "On Foot Navigation: When GPS alone is not Enough", Journal of Navigation, vol. 53, No. 2, Sep. 2000, pp. 279-285 (6 pages).

Lammel et al., "Indoor Navigation with MEMS Sensors", Proceedings of the Eurosensors XIII conference, vol. 1, No. 1, Sep. 2009, pp. 532-535 (4 pages).

Lester et al, "Validated caloric expenditure estimation using a single body-worn sensor", Proc. of the Int'l Conf. on Ubiquitous Computing, 2009, pp. 225-234 (10 pages).

Lester et al., "A Hybrid Discriminative/Generative Approach for Modeling Human Activities", Proc. of the Int'l Joint Conf. Artificial Intelligence, 2005, pp. 766-772 (7 pages).

Ohtaki et al, "Automatic classification of ambulatory movements and evaluation of energy consumptions utilizing accelerometers and barometer", Microsystem Technologies, vol. 11, No. 8-10, Aug. 2005, pp. 1034-1040 (7 pages).

Parkka, et al, Activity Classification Using Realistic Data From Wearable Sensors, IEEE Transactions on Information Technology in Biomedicine, vol. 10, No. 1, Jan. 2006, pp. 119-128 (10pages).

PCT/IB07/03617 International Search Report issued on Aug. 15, 2008, 3 pages.

Perrin et al, "Improvement of Walking Speed Prediction by Accelerometry and Altimetry, Validated by Satellite Positioning", Medical & Biological Engineering & Computing, vol. 38, 2000, pp. 164-168 (5 pages).

Retscher, "An Intelligent Multi-Sensor system for Pedestrian Navigation", Journal of Global Positioning Systems, vol. 5, No. 1, 2006, pp. 110-118 (9 pages).

(56) References Cited

OTHER PUBLICATIONS

Sagawa et al, "Classification of Human Moving Patterns Using Air Pressure and Acceleration", Proceedings of the 24th Annual Conference of the IEEE Industrial Electronics Society, vol. 2, Aug.-Sep. 1998, pp. 1214-1219 (6 pages).
Sagawa et al, "Non-restricted measurement of walking distance", IEEE Int'l Conf. on Systems, Man, and Cybernetics, vol. 3, Oct. 2000, pp. 1847-1852 (6 pages).
Specification of the Bluetooth® System, Core Package, version 4.1, Dec. 2013, vols. 0 & 1, 282 pages.
Stirling et al., "Evaluation of a New Method of Heading Estimation of Pedestrian Dead Reckoning Using Shoe Mounted Sensors", Journal of Navigation, vol. 58, 2005, pp. 31-45 (15 pages).
Suunto LUMI, "User Guide", Copyright Jun. and Sep. 2007, 49 pages.
Tanigawa et al, "Drift-Free Dynamic Height Sensor Using MEMS IMU Aided by MEMS Pressure Sensor", Workshop on Positioning, Navigation and Communication, Mar. 2008, pp. 191-196 (6 pages).
VTI Technologies, "SCP 1000-D01/D11 Pressure Sensor as Barometer and Altimeter", Application Note 33, Jun. 2006, 3 pages.
"Activator is One of the Best Cydia iPhone Hacks I Control your iPhone with Gestures," IPHONE-TIPS-AND-ADVICE.COM, [retrieved on Jul. 9, 2013 at http://www.iphone-tips-and-advice.comlactivatior.html], 10 pp.
"Parts of Your Band," (Product Release Date Unknown, downloaded Jul. 22, 2013) Jawbone UP Band, 1 page.
Chudnow, Alan (Dec. 3, 2012) "Basis Wristband Make Its Debut," The Wired Self, Living in a Wired World, published in Health [retrieved on Jul. 22, 2013 at http://thewiredself.com/health/basis-wrist-band-make-its-debut/], 3pp.
Definition of "Graphic" from Merriam-Webster Dictionary, downloaded from merriam-webster.com on Oct. 4, 2014, 3 pp.
Definition of "Graphical user interface" from Merriam-Webster Dictionary, downloaded from merriam-webster.com on Oct. 4, 2014, 2 pp.
DesMarais, Christina (posted on Sep. 3, 2013) "Which New Activity Tracker is Best for You?" Health and Home, Health & Fitness, Guides & Reviews, [Retrieved on Sep. 23, 2013 at http://www.techlicious.com/guide/which-new-activity-tracker-is-right-for--you/] 4 pp.
Empson, Rip, (Sep. 22, 2011) "Basis Reveals an Awesome New Affordable Heart and Health Tracker You Can Wear on Your Wrist," [retrieved on Sep. 23, 2013 at http://techcrunch.com/2011/09/22/basis-reveals-an-awesome-new . . . ], 3 pp.
Fitbit User's Manual, Last Updated Oct. 22, 2009, 15 pages.
Forerunner® 10 Owner's Manual (Aug. 2012), Garmin Ltd., 10 pp.
Forerunner® 110 Owner's Manual, (2010) "GPS-Enabled Sport Watch," Garmin Ltd., 16 pp.
Forerunner® 201 personal trainer owner's manual, (Feb. 2006) Garmin Ltd., 48 pp.
Forerunner® 205/305 Owner's Manual, GPS-enabled trainer for runners, (2006-2008), Garmin Ltd., 80 pp.
Forerunner® 210 Owner's Manual, (2010) "GPS-Enabled Sport Watch," Garmin Ltd., 28 pp.
Forerunner® 301 personal trainer owner's manual, (Feb. 2006) Garmin Ltd., 66 pp.
Forerunner® 310XT Owner's Manual, Multisport GPS Training Device, (2009-2013), Garmin Ltd., 56 pp.
Forerunner® 405 Owner's Manual, (Mar. 2011) "GPS-Enabled Sport Watch With Wireless Sync," Garmin Ltd., 56 pp.
Forerunner® 405CX Owner's Manual, "GPS-Enabled Sports Watch With Wireless Sync," (Mar. 2009), Garmin Ltd., 56 pp.
Forerunner® 410 Owner's Manual, (Jul. 2012) "GPS-Enabled Sport Watch With Wireless Sync," Garmin Ltd., 52 pp.
Forerunner® 50 with ANT+Sport.TM. wireless technology, Owner's Manual, (Nov. 2007) Garmin Ltd., 44 pp.
Forerunner® 910XT Owner's Manual, (Jan. 2013) Garmin Ltd., 56 pp.
Garmin Swim™ Owner's Manual (Jun. 2012), 12 pp.
Lark/Larkpro, User Manual, (2012) "What's in the box," Lark Technologies, 7 pp.
Larklife, User Manual, (2012) Lark Technologies, 7 pp.
Minetti et al. Energy cost of walking and running at extreme uphill and downhill slopes. J Appl Physiol. 2002; 93:10/39/1046.
Nike+ FuelBand GPS Manual, User's Guide (Product Release Date Unknown, downloaded Jul. 22, 2013), 26 pp.
Nike+SportBand User's Guide, (Product Release Date Unknown, downloaded Jul. 22, 2013), 36 pages.
Nike+SportWatch GPS Manual, User's Guide, Powered by TOMTOM, (Product Release Date Unknown, downloaded Jul. 22, 2013), 42 pages.
O'Donovan et al., 2009, A context aware wireless body area network (BAN), Proc. 3rd Intl. Conf. Pervasive Computing Technologies for Healthcare, pp. 1-8.
Polar WearLink® + Coded Transmitter 31 Coded Transmitter W.I.N.D. User Manual, Polar® Listen to Your Body, Manufactured by Polar Electro Oy, 11 pages.
Rainmaker, (Jun. 25, 2012, updated Feb. 16, 2013) "Garmin Swim watch In-Depth Review," [retrieved on Sep. 9, 2013 at http://www.dcrainmaker.com/2012/06/garmin-swim-in-depth-review.html, 38 pp.
Thompson et al., (Jan. 1996) "Predicted and measured resting metabolic rate of male and female endurance athletes," Journal of the American Dietetic Association 96(1):30-34.

\* cited by examiner

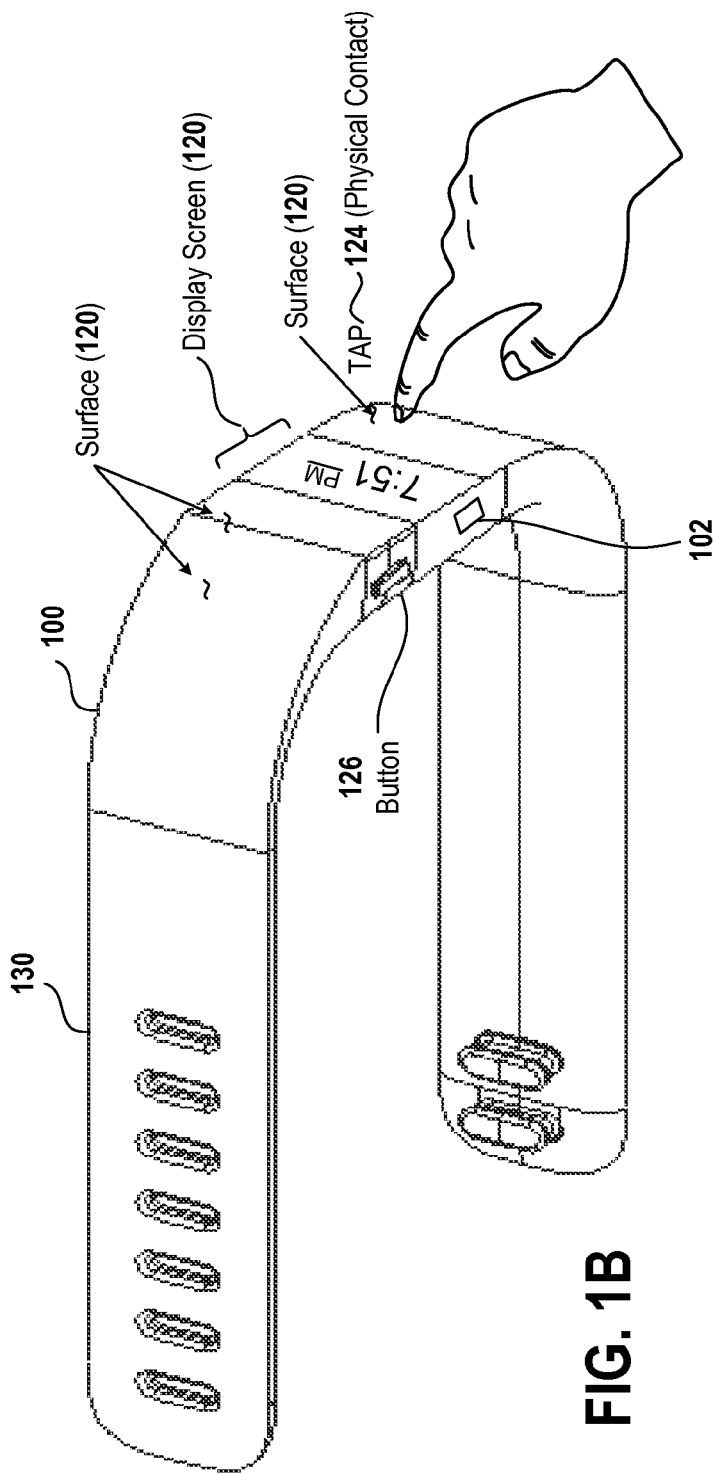
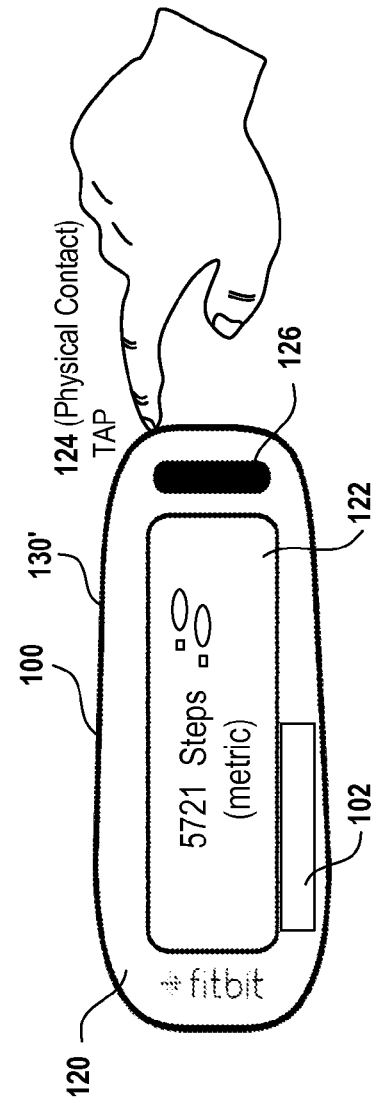
FIG. 1B
FIG. 1C

ALARM SETTING AND INTERFACING WITH GESTURE CONTACT INTERFACING CONTROLS

CLAIM OF PRIORITY

This application is a continuation of U.S. patent application Ser. No. 14/329,735, filed on Jul. 11, 2014, entitled "Alarm Setting and Interfacing with Gesture Contact Interfacing Controls," which is a continuation of U.S. patent application Ser. No. 14/050,305, now U.S. Pat. No. 8,812,259, entitled "Alarm Setting and Interfacing with Gesture Contact Interfacing Controls," filed on Oct. 9, 2013, which claims priority to U.S. Provisional Application No. 61/886,000, entitled "Alarm Setting and Interfacing with Gesture Contact Interfacing Controls," filed on Oct. 2, 2013, the disclosures of all of which are incorporated by reference herein for all purposes.

CROSS REFERENCE TO RELATED APPLICATION

This application is related to U.S. application Ser. No. 14/050,292, now U.S. Pat. No. 8,744,803, filed on Oct. 9, 2013, entitled "Methods, Systems, and Devices for Activity Tracking Device Data Synchronization with Computing Devices," which claims priority to U.S. Provisional Application No. 61/885,962, filed on Oct. 2, 2013, both of which are incorporated herein by reference for all purposes.

FIELD

The present disclosure relates to systems and methods for capturing activity data over a period of time and methods and systems for configuring alarm settings in activity tracking devices.

BACKGROUND

In recent years, the need for health and fitness has grown tremendously. The growth has occurred due to a better understanding of the benefits of good fitness to overall health and wellness. Unfortunately, although today's modern culture has brought about many new technologies, such as the Internet, connected devices and computers, people have become less active. Additionally, many office jobs require people to sit in front of computer screens for long periods of time, which further reduces a person's activity levels. Furthermore, much of today's entertainment options involve viewing multimedia content, computer social networking, and other types of computer involved interfacing. Although such computer activity can be very productive as well as entertaining, such activity tends to reduce a person's overall physical activity.

To provide users concerned with health and fitness a way of measuring or accounting for their activity or lack thereof, fitness trackers are often used. Fitness trackers are used to measure activity, such as walking, motion, running, sleeping, being inactive, bicycling, exercising on an elliptical trainer, and the like. Usually, the data collected by such fitness trackers can be transferred and viewed on a computing device. However, such data is often provided as a basic accumulation of activity data with complicated or confusing interfaces.

It is in this context that embodiments described herein arise.

SUMMARY

Embodiments described in the present disclosure provide systems, apparatus, computer readable media, and methods for configuring alarm setting for activity tracking devices using remote computing devices and transferring the configured alarm settings to the activity tracking devices. Some embodiments are directed toward the use of contact gestures either to transition an alarm of the activity tracking device into a snooze mode or to turn the alarm off.

In one embodiment, a method, which is executed by a processor, is provided. The method includes receiving an alarm setting that defines a time of day for triggering an alarm on a device for tracking activity data of a user, and activating the alarm upon reaching the time of day defined by the alarm setting. The alarm produces a vibration of the device. The method further includes determining a level of activity of the user detected by the device for tracking activity data of the user when the alarm is activated, and automatically deactivating the alarm if the level of activity qualifies for deactivating the alarm. The deactivating of the alarm causes the vibration of the device to be suspended.

In one embodiment, the level of activity that qualifies for deactivating the alarm is a predetermined number of steps. In one embodiment, the predetermined number of steps is detected after the alarm is activated. In one embodiment, the predetermined number of steps is detected during a period of time that includes a time period before the alarm is activated.

In another embodiment, a device configured for capture of activity data for a user is provided. The device includes a housing, a sensor, a motor, a memory, and a processor. The sensor is disposed in the housing to track activity data of the user. The motor causes vibration of the housing of the device. The memory stores an alarm setting that defines a time of day for triggering an alarm on the device. The processor activates the alarm upon reaching the time of day defined by the alarm setting, with the alarm causing the motor to produce the vibration of the housing. The sensor, which is interfaced with the processor, is configured to detect a current level of activity of the user. The processor is configured to automatically deactivate the alarm if the current level of activity qualifies for deactivating the alarm. The deactivating of the alarm causes the vibration of the device to be suspended.

In yet another embodiment, one or more non-transitory computer readable media are provided. The one or more computer readable media include instructions which, when executed by a processor, perform the following operations: receive an alarm setting that defines a time of day for triggering an alarm on a device for tracking activity data of a user; activate the alarm upon reaching the time of day defined by the alarm setting, the alarm producing a vibration of the device; determine a level of activity of the user detected by the device for tracking activity data of the user when the alarm is activated; and automatically deactivate the alarm if the level of activity qualifies for deactivating the alarm, the deactivating of the alarm causing the vibration of the device to be suspended. In one embodiment, the vibration being suspended transitions the alarm into the off mode.

In one embodiment, a method, which is executed by a processor, is provided. The method includes receiving an alarm setting that defines a time of day for triggering an alarm on a device for tracking activity data of a user, and activating the alarm upon reaching the time of day defined by the alarm setting. The alarm produces a vibration of the activity tracking device. The method further includes using a sensor to detect a physical contact upon the device, and deactivating the alarm if the physical contact qualifies as an input to deactivate the alarm. The deactivating of the alarm causes the vibration of the activity tracking device to be suspended.

In one embodiment, the suspension of the vibration of the activity tracking device transitions the alarm into either a snooze mode or an off mode. In one embodiment, the snooze mode continues for a predetermined period of time before reactivating the alarm. In one embodiment, the method further includes transitioning into the snooze mode one or more times until entering the off mode or processing the vibration for a threshold period of time.

In one embodiment, the physical contact is a result of one or more taps on a surface of the activity tracking device. In one embodiment, a snooze mode, which causes the vibration to be suspended, is entered when the physical contact is represented by a single tap onto a surface of the activity tracking device, or a double tap onto the surface of the device, or three taps onto the surface of the device, or four taps onto the surface of the device, or a predetermined set of repeated taps onto the surface of the device. In one embodiment, two or more of the taps are received within a predetermined period of time to qualify as an input.

In one embodiment, the method further includes transitioning from the snooze mode to an off mode when an additional physical contact is sensed by the sensor. The additional physical contact can be represented by a single tap onto a surface of the activity tracking device, or a double tap onto the surface of the device, or three taps onto the surface of the device, or four taps onto the surface of the device, or a predetermined set of repeated taps onto the surface of the device. In one embodiment, two or more of the taps are received within a predetermined period of time to qualify as an input.

In one embodiment, the method further includes transitioning from the snooze mode to an off mode when the processor of the activity tracking device determines that a button of the device is pressed.

In one embodiment, the alarm setting is received wirelessly from a computing device. In one embodiment, the computing device has access to the Internet. In one embodiment, the alarm setting is programmable at a website managed by a server, and the website is managed by the server to allow access to user accounts, with each user account having associated therewith one or more of the activity tracking devices, such that the alarm setting is custom set in a user account In one embodiment, the alarm setting is transferred from the server to the computing device over the Internet and from the computing device to the device via a wireless Bluetooth connection. In one embodiment, the activity data of the user includes metrics associated with one or more of step count metrics, or stair count metrics, or distance traveled metrics, or active time metrics, or calories burned metrics, or sleep metrics.

In another embodiment, a device configured for capture of activity data for a user is provided. The device includes a housing, a sensor, a motor, a memory, and a processor. The sensor is disposed in the housing to capture physical contact upon the housing. The motor causes vibration of the housing of the device. The memory stores an alarm setting that defines a time of day for triggering an alarm on the device. The processor activates the alarm upon reaching the time of day defined by the alarm setting, with the alarm causing the motor to produce the vibration of the housing. The sensor, which is interfaced with the processor, is configured to detect a physical contact upon the housing of the device. The processor is configured to deactivate the alarm if the physical contact qualifies as an input to deactivate the alarm. The deactivating of the alarm causes the vibration of the device to be suspended.

In one embodiment, the housing is part of a wearable wrist attachable structure, or an attachable structure that can be carried or worn by the user. In one embodiment, the wearable wrist attachable structure is defined at least partially from a plastic material. In one embodiment, the physical contact captured by the sensor is from one or more taps upon the housing by a finger or hand. In one embodiment, the housing includes a button, and the physical contact upon the housing of the device is not from a button press.

In one embodiment, the housing further includes wireless communication logic. In one embodiment, the wireless communication logic includes one of WiFi processing logic, or Bluetooth (BT) processing logic, or radio processing logic. In one embodiment, the wireless communication logic is configured to pair with a portable computing device or a computer, and the portable computing device or the computer is configured for communication over the Internet with a server, the server having processing instructions for configuring the alarm settings.

In one embodiment, the processor examines predefined motion profiles captured by the sensor to qualify the physical contact as the input, such that motion profiles outside of the predetermined motion profiles do not qualify as the input. In one embodiment, suspending the vibration of the device transitions the alarm into one of a snooze mode or an off mode. In one embodiment, the processor configures the snooze mode to continue for a predetermined period of time before reactivating the alarm, and the processor transitions into the snooze mode one or more times until entering the off mode or processing the vibration for a threshold period of time.

In one embodiment, the physical contact is the result of one or more taps on a surface of the device. In one embodiment, two or more of the taps are received within a predetermined period of time to qualify as the input. In one embodiment, the processor causes a snooze mode, which causes the vibration to be suspended, to be entered when the physical contact is represented by a single tap onto a surface of the device, or a double tap onto the surface of the device, or three taps onto the surface of the device, or four taps onto the surface of the device, or a predetermined set of repeated taps onto the surface of the device.

In yet another embodiment, one or more non-transitory computer readable media are provided. The one or more computer readable media include instructions which, when executed by a processor, perform the following operations: receiving an alarm setting that defines a time of day for triggering an alarm on a device for tracking activity data of a user; activating the alarm upon reaching the time of day defined by the alarm setting, the alarm producing a vibration of the device; using a sensor to detect a physical contact upon the device; and deactivating the alarm if the physical contact qualifies as an input to deactivate the alarm, the deactivating causing the vibration of the device to be suspended.

Other aspects will become apparent from the following detailed description, taken in conjunction with the accompanying drawings, illustrating by way of example the principles of embodiments described in the present disclosure.

BRIEF DESCRIPTION OF THE DRAWINGS

Various embodiments described in the present disclosure may best be understood by reference to the following description taken in conjunction with the accompanying drawings in which:

FIG. 1B illustrates an example of an activity tracking device, in accordance with one embodiment of the present invention.

FIG. 1C illustrates another example of an activity tracking device, in accordance with one embodiment of the present invention.

DETAILED DESCRIPTION

Embodiments described in the present disclosure provide systems, apparatus, computer readable media, and methods for configuring alarm setting for activity tracking devices using remote computing devices and transferring the configured alarm settings to the activity tracking devices. Some embodiments are directed toward the use of contact gestures either to transition an alarm of the activity tracking device into a snooze mode or to turn the alarm off.

It should be noted that there are many inventions described and illustrated herein. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

Further, in the course of describing and illustrating the present inventions, various circuitry, architectures, structures, components, functions and/or elements, as well as combinations and/or permutations thereof, are set forth. It should be understood that circuitry, architectures, structures, components, functions and/or elements other than those specifically described and illustrated, are contemplated and are within the scope of the present inventions, as well as combinations and/or permutations thereof.

Figure 1A:
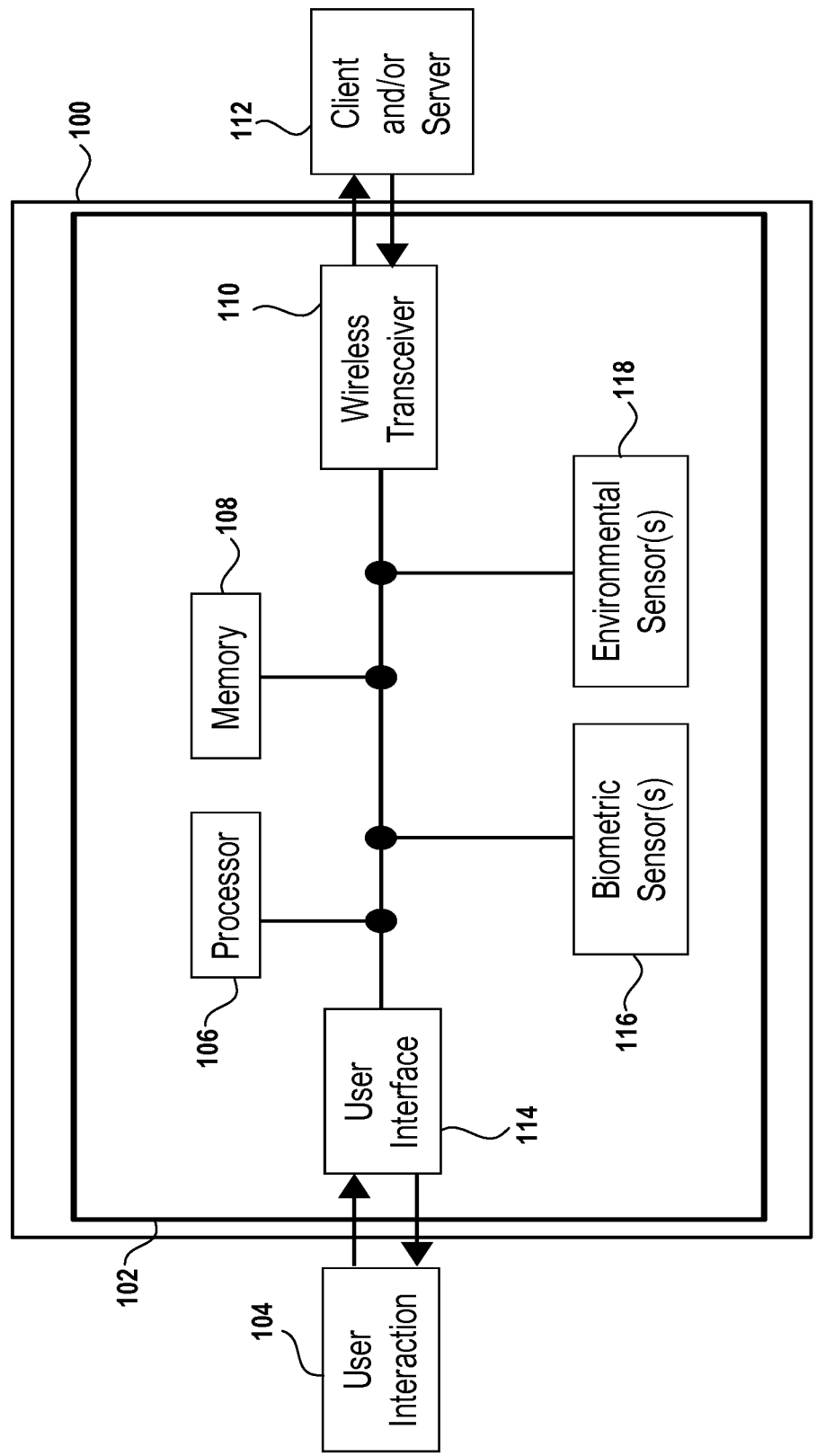
FIG. 1A shows a block diagram of an activity tracking device, in accordance with one embodiment of the present invention.

FIG. 1A shows a block diagram of an activity tracking device 100, in accordance with one embodiment of the present invention. The activity tracking device 100 is contained in a housing, which may be worn or held by a user. The housing may be in the form of a wristband, a clip on device, a wearable device, or may be held by the user either in the user's hand or in a pocket or attached to the user's body. The activity tracking device 100 includes device components 102, which may be in the form of logic, storage, and glue logic, one or more processors, microelectronics, and interfacing circuitry. In one example, the components 102 will include a processor 106, memory 108, a wireless transceiver 110, a user interface 114, biometric sensors 116, and environmental sensors 118.

The environmental sensors 118 may be in the form of motion detecting sensors. In some embodiments, a motion sensor can be one or more of an accelerometer, or a gyroscope, or a rotary encoder, or a calorie measurement sensor, or a heat measurement sensor, or a moisture measurement sensor, or a displacement sensor, or an ultrasonic sensor, or a pedometer, or an altimeter, or a linear motion sensor, or an angular motion sensor, or a multi-axis motion sensor, or a combination thereof. The biometric sensors 116 can be defined to measure physiological characteristics of the user that is using the activity tracking device 100. The user interface 114 provides a way for communicating with the activity tracking device 100, in response to user interaction 104. The user interaction 104 can be in the form of physical contact (e.g., without limitation, tapping, sliding, rubbing, multiple taps, gestures, etc.).

In some embodiments, the user interface 114 is configured to receive user interaction 104 that is in the form of noncontact input. The noncontact input can be by way of proximity sensors, button presses, touch sensitive screen inputs, graphical user interface inputs, voice inputs, sound inputs, etc. The activity tracking device 100 can communicate with a client and/or server 112 using the wireless transceiver 110. The wireless transceiver 110 will allow the activity tracking device 100 to communicate using a wireless connection, which is enabled by wireless communication logic. The wireless communication logic can be in the form of a circuit having radio communication capabilities. The radio communication capabilities can be in the form of a Wi-Fi connection, a Bluetooth connection, a low-energy Bluetooth connection, or any other form of wireless tethering or near field communication. In still other embodiments, the activity tracking device 100 can communicate with other computing devices using a wired connection (not shown). As mentioned, the environmental sensors 118 can detect motion of the activity tracking device 100.

The motion can be activity of the user, such as walking, running, stair climbing, etc. The motion can also be in the form of physical contact received on any surface of the activity tracking device 110, so long as the environmental sensors 118 can detect such motion from the physical contact. As will be explained in more detail below, the physical contact may be in the form of a tap or multiple taps by a finger upon the housing of the activity tracking device 100.

FIG. 1B illustrates an example of an activity tracking device 100 having a housing 130 in the form of a wearable wrist attachable device. The sensors of the activity tracking device 100 can, as mentioned above, detect motion such as physical contact that is applied and received on a surface 120 of the housing 130. In the example shown, the physical contact 124 is in the form of a tap or multiple taps on the surface 120. Device components 102 are, in one embodiment, contained within the housing 130. The location at which the device components 102 are integrated into the housing 130 can vary. For example, the device components 102 can be integrated throughout various locations around the housing 130, and not limited to the central portion of the wrist attachable device. In some embodiments, the device components 102 can be integrated into or with a smart watch device.

In other embodiments, the device components 102 are positioned substantially in a central position of the wrist attachable device, such as under or proximate to a location where a display screen 122 is located. In the illustrated example, the housing 130 also includes a button 126. The button 126 can be pressed to activate the display screen 122, navigate to various metrics displayed on the screen 122, or turn off the screen 122.

FIG. 1C illustrates another example of an activity tracking device 100, in accordance with one embodiment of the present invention. The form factor of the activity tracking device 100 is shown as a clickable device that includes a screen 122, a button 126, and device components 102 integrated within the housing 130'. The housing 130' can include a clip that allows for attachment to clothing or articles of the user, or to simply place the device within a pocket or holder of the user. Accordingly, the physical contact 124 shown with respect to FIG. 1B can also be implemented upon the surface 120 of activity tracking device 100 of FIG. 1C. It should be understood, therefore, that the form factor of the activity tracking device 100 can take on various configurations and should not be limited to the example configurations provided herein.

Figure 2A:
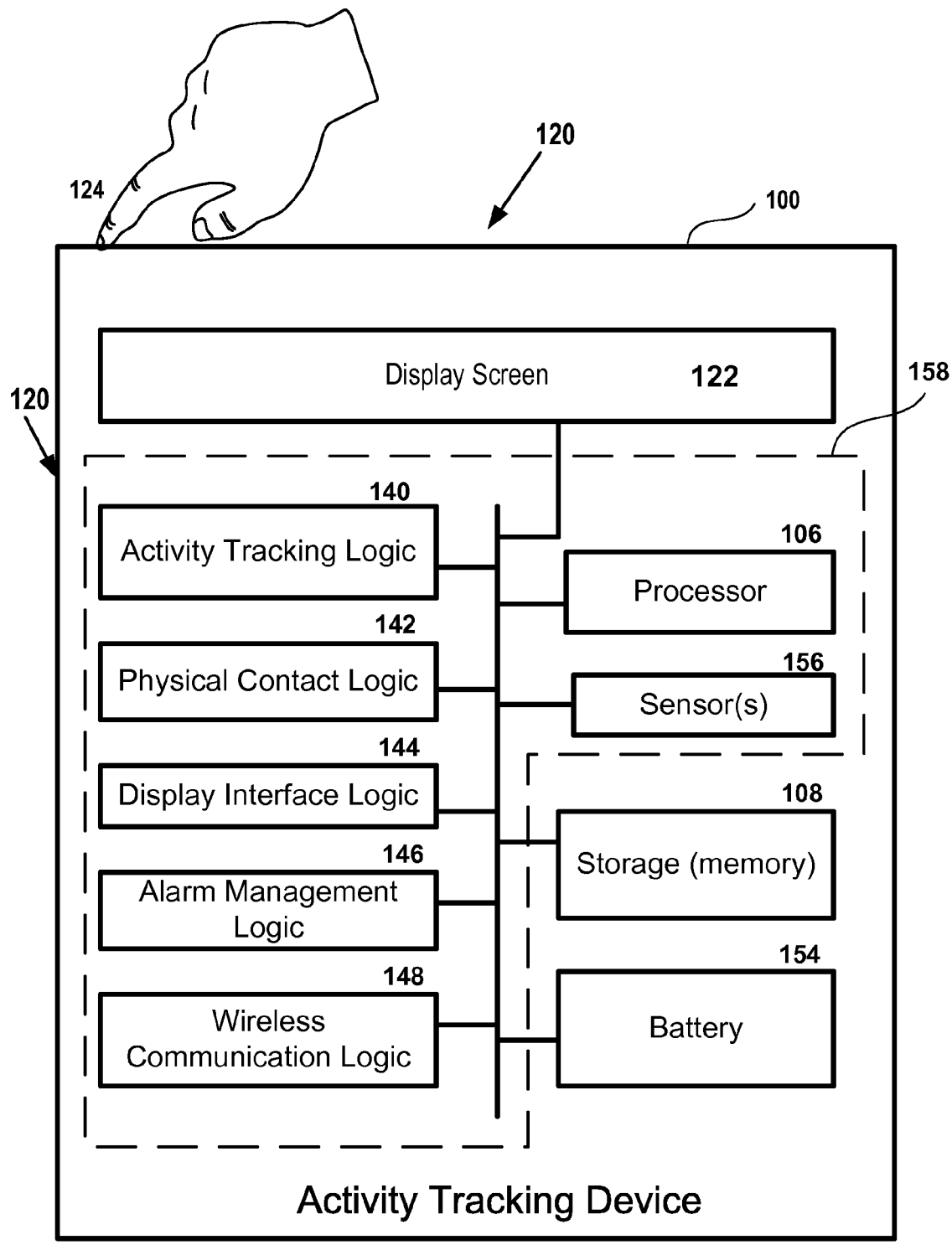
FIG. 2A illustrates an example of activity tracking device including example components utilized for tracking activity and motion of the device, and associated interfaces to a display screen, in accordance with one embodiment of the present invention.

FIG. 2A illustrates an example of activity tracking device 100 of FIG. 1A, showing some additional example components utilized for tracking activity and motion of the device, and associated interfaces to display screen 122. In this example, the finger of a user can be used to tap and provide physical contact 124 onto any surface 120 of activity tracking device 100. The physical contact, when sensed by sensors 156 of the activity tracking device 100, will cause a response by the activity tracking device 100, and therefore provide some metric on the display screen 122. In one embodiment, examples of a display screen 122 can include, but are not limited to, liquid crystal display (LCD) screens, light emitting diode (LED) screens, organic light emitting diode (OLED) screens, plasma display screens, etc.

As shown in FIG. 2A, the activity tracking device 100 includes logic 158. Logic 158 may include activity tracking logic 140, physical contact logic 142, display interface logic 144, alarm management logic 146, wireless communication logic 148, processor 106, and sensors 156. Additionally, storage (e.g. memory) 108, and a battery 154 can be integrated within the activity tracking device 100. The activity tracking logic 140 can include logic that is configured to process motion data produced by sensors 156, so as to quantify the motion and produce identifiable metrics associated with the motion.

Some motions will produce and quantify various types of metrics, such as step count, stairs climbed, distance traveled, very active minutes, calories burned, etc. The physical contact logic 142 can include logic that calculates or determines when particular physical contact can qualify as an input. To qualify as an input, the physical contact detected by sensors 156 should have a particular pattern that is identifiable as input. For example, the input may be predefined to be a double tap input, and the physical contact logic 142 can analyze the motion to determine if a double tap indeed occurred in response to analyzing the sensor data produced by sensors 156.

In other embodiments, the physical contact logic can be programmed to determine when particular physical contacts occurred, the time in between the physical contacts, and whether the one or more physical contacts will qualify within predefined motion profiles that would indicate that an input is desired. If physical contact occurs that is not within some predefined profile or pattern, the physical contact logic will not indicate or qualify that physical contact as an input.

The display interface logic 144 is configured to interface with the processor and the physical contact logic to determine when specific metric data will be displayed on the display screen 122 of the activity tracking device 100. The display interface logic 144 can act to turn on the screen, display metric information, display characters or alphanumeric information, display graphical user interface graphics, or combinations thereof. Alarm management logic 146 can function to provide a user interface and settings for managing and receiving input from a user to set an alarm. The alarm management logic can interface with a timekeeping module (e.g., clock, calendar, time zone, etc.), and can trigger the activation of an alarm. The alarm can be in the form of an audible alarm or a non-audible alarm.

A non-audible alarm can provide such alarm by way of a vibration. The vibration can be produced by a motor integrated in the activity tracking device 100. The vibration can be defined to include various vibration patterns, intensities, and custom set patterns. The vibration produced by the motor or motors of the activity tracking device 100 can be managed by the alarm management logic 146 in conjunction with processing by the processor 106. The wireless communication logic 148 is configured for communication of the activity tracking device with another computing device by way of a wireless signal. The wireless signal can be in the form of a radio signal. As noted above, the radio signal can be in the form of a Wi-Fi signal, a Bluetooth signal, a low energy Bluetooth signal, or combinations thereof. The wireless communication logic can interface with the processor 106, storage 108 and battery 154 of device 100, for transferring activity data, which may be in the form of motion data or processed motion data, stored in the storage 108 to the computing device.

In one embodiment, processor 106 functions in conjunction with the various logic components 140, 142, 144, 146, and 148. The processor 106 can, in one embodiment, provide the functionality of any one or all of the logic components. In other embodiments, multiple chips can be used to separate the processing performed by any one of the logic components and the processor 106. Sensors 156 can communicate via a bus with the processor 106 and/or the logic components. The storage 108 is also in communication with the bus for providing storage of the motion data processed or tracked by the activity tracking device 100. Battery 154 is provided for providing power to the activity tracking device 100.

Figure 2B:
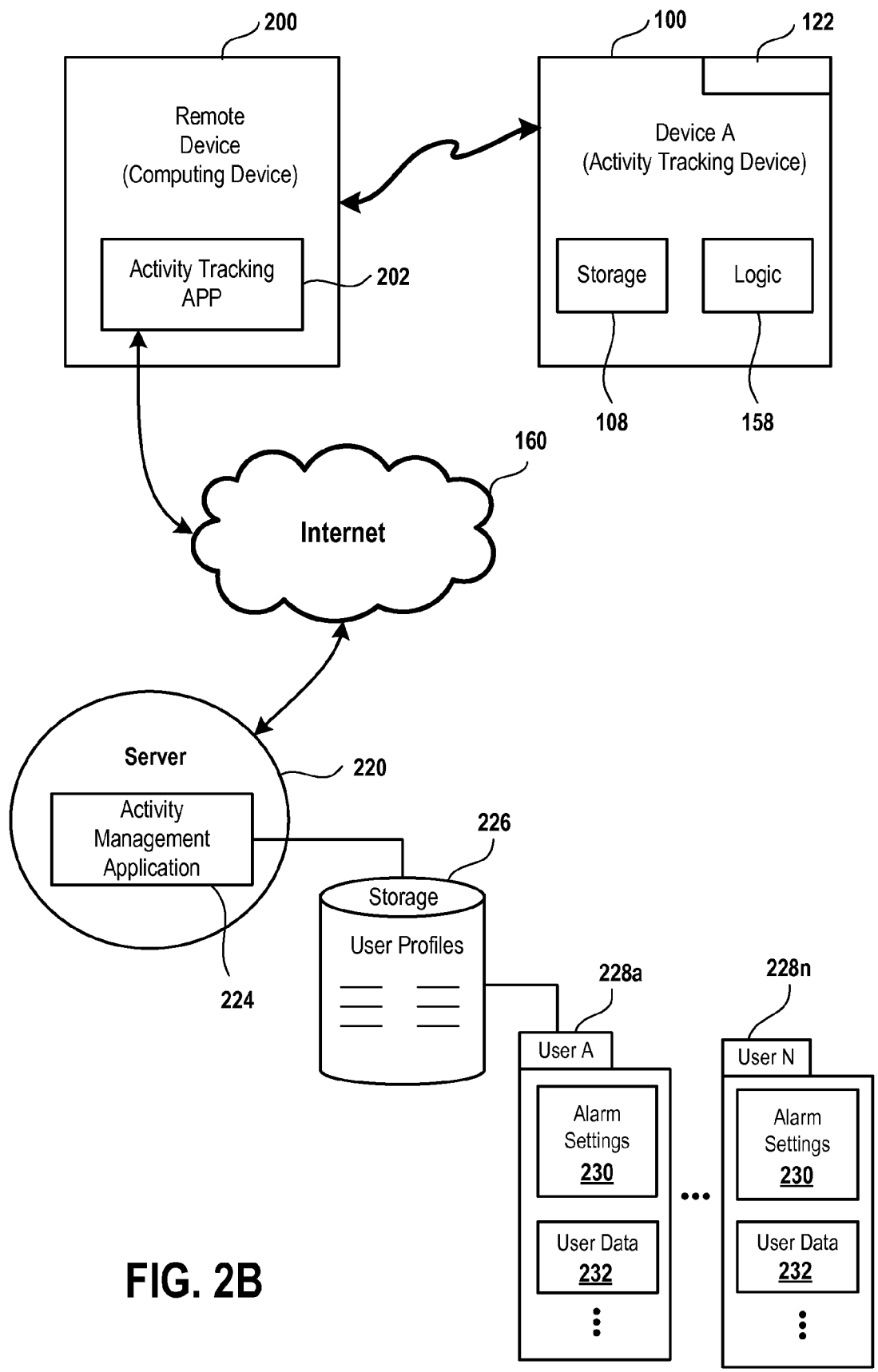
FIG. 2B illustrates an example of activity tracking device in communication with a remote device, in accordance with one embodiment of the present invention.

FIG. 2B illustrates an example of activity tracking device 100 in communication with a remote device 200. Remote device 200 is a computing device that is capable of communicating wirelessly with activity tracking device 100 and with the Internet 160. Remote device 200 can support installation and execution of applications. Such applications can include an activity tracking application 202. Activity tracking application 202 can be downloaded from a server. The server can be a specialized server or a server that provides applications to devices, such as an application store. Once the activity tracking application 202 is installed in the remote device 200, the remote device 200 can communicate or be set to communicate with activity tracking device 100 (Device A). The remote device 200 can be a smartphone, a handheld computer, a tablet computer, a laptop computer, a desktop computer, or any other computing device capable of wirelessly interfacing with Device A and the Internet.

In one embodiment, remote device 200 communicates with activity tracking device 100 over a Bluetooth connection. In one embodiment, the Bluetooth connection is a low energy Bluetooth connection (e.g., Bluetooth LE, BLE, or Bluetooth Smart). Low energy Bluetooth is configured for providing low power consumption relative to standard Bluetooth circuitry. Low energy Bluetooth uses, in one embodiment, a 2.4 GHz radio frequency, which allows for dual mode devices to share a single radio antenna. In one embodiment, low energy Bluetooth connections can function at distances up to 50 meters, with over the air data rates ranging between 1-3 megabits (Mb) per second. In one embodiment, a proximity distance for communication can be defined by the particular wireless link, and is not tied to any specific standard. It should be understood that the proximity distance limitation will change in accordance with changes to existing standards and in view of future standards and/or circuitry and capabilities.

Remote device 200 can also communicate with the Internet 160 using an Internet connection. The Internet connection of the remote device 200 can include cellular connections, wireless connections such as Wi-Fi, and combinations thereof (such as connections to switches between different types of connection links). The remote device, as mentioned above, can be a smartphone or tablet computer, or any other type of computing device having access to the Internet and with capabilities for communicating with the activity tracking device 100.

A server 220 is also provided, which is interfaced with the Internet 160. The server 220 can include a number of applications that service the activity tracking device 100, and the associated users of the activity tracking device 100 by way of user accounts. For example, the server 220 can include an activity management application 224. The activity management application 224 can include logic for providing access to various devices 100, which are associated with user accounts managed by server 220. Server 220 can include storage 226 that includes various user profiles associated with the various user accounts. The user account 228a for user A and the user account 228n for user N are shown to include various information.

The information in a user account can include, without limitation, data associated with alarm settings 230, user data, etc. As will be described in more detail below, the alarm settings 230 include information regarding a user's preferences, settings, and configurations which are settable by the user or set by default at the server 220 when accessing a respective user account. The storage 226 will include any number of user profiles, depending on the number of registered users having user accounts for their respective activity tracking devices. It should also be noted that a single user account can have various or multiple devices associated therewith, and the multiple devices can be individually customized, managed, and accessed by a user. In one embodiment, the server 220 provides access to a user to view the user data 232 associated with an activity tracking device.

Figure 3:
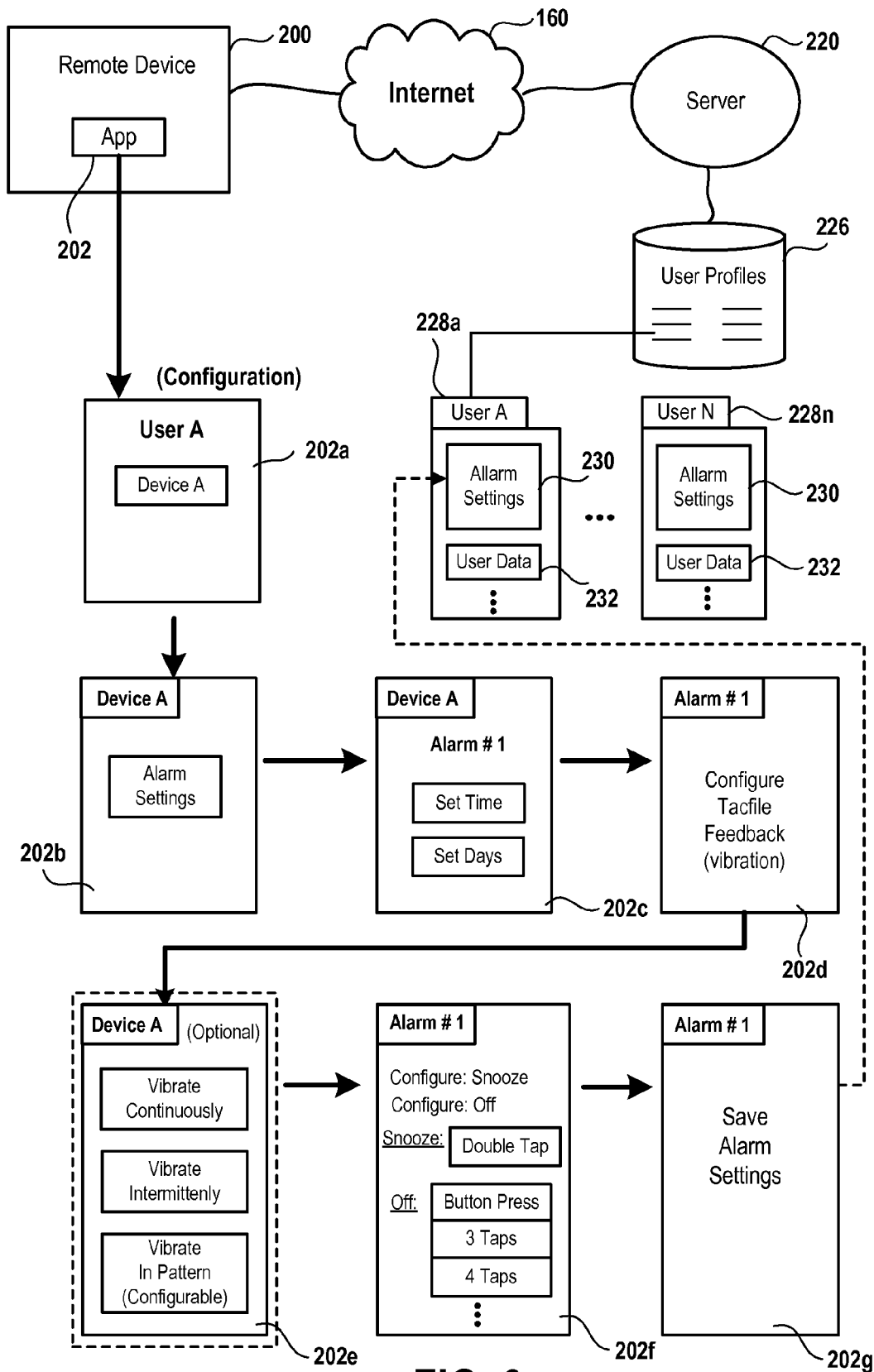
FIG. 3 is a block diagram that illustrates the configuring of alarm settings for an activity tracking device, in accordance with one embodiment of the present invention.

FIG. 3 is a block diagram that illustrates the configuring of alarm settings for an activity tracking device 100, in accordance with one embodiment of the present invention. As described above, remote device 200, e.g., a smartphone or a tablet computing device, is provided with activity tracking application 202. Both remote device 200 and also server 220 can communicate with Internet 160. Server 220 can include storage 226 that includes various user profiles associated with various user accounts. The information in the user accounts can include, among other data, data associated with alarm settings 230.

To enable a user to configure the alarm settings for an activity tracking device 100 using remote device 200, activity tracking application 202 provides a number of interfaces that allow the user to configure the alarm settings. In one embodiment, the activity tracking application 202 displays a view 202a that shows the activity tracking devices associated with the user's account. As shown in view 202a, only "Device A" is associated with User A's account. It should be appreciated, however, that additional activity tracking devices, e.g., Device B, Device C, etc., also could be associated with a user's account. A suitable GUI control, e.g., a graphic icon that can be activated by a finger touch or other user input, is used to identify each device associated with the user's account, e.g., Device A, Device B, etc., so that the user can select the device for which the alarm settings are to be configured. In the example shown in view 202a, the user would touch the "Device A" GUI control to select that device for configuration.

Once the particular device to be configured has been selected, the activity tracking application 202 displays a view 202b that shows the settings available to be selected for configuration. As shown in view 202b, only "Alarm Settings" are available to be selected for configuration. It should be appreciated, however, that other settings also could be displayed. In the example shown in view 202b, the user would touch the "Alarm Settings" GUI control to select those settings for configuration. As shown in view 202c, the activity tracking application 202 then provides GUI controls that allow the user to proceed to set an alarm time ("Set Time") and to select the days on which the alarm is to be active ("Set Days"). In the event the user touches the "Set Time" GUI control, the activity tracking application 202 displays a further view (not shown) that allows the user to set an alarm time, e.g., 6:30 am, 7:30 am, etc. In the event the user touches the "Set Days" GUI control, the activity tracking application 202 displays a further view (not shown) that allows the user to set the days on which the alarm is to be active, e.g., Monday, Tuesday, Monday thru Friday (weekdays), etc. It should be appreciated that more than one alarm, e.g., Alarm #1, Alarm #2, Alarm #3, etc., can be configured in this manner.

Once the time and days for an alarm have been set, the activity tracking application 202 provides GUI controls that allow a user to select either an audible alarm or a non-audible alarm. The non-audible alarm can be produced by tactile feedback, e.g., vibration, generated by a motor for causing vibration of the housing of the activity tracking device. The vibration can be a default vibration set by the system or, optionally, a vibration that is configured by the user. In the example shown in view 202d, the activity tracking application 202 displays a GUI control that allows the user to configure the tactile feedback (e.g., vibration) used to produce a non-audible alarm. The activity tracking application 202 then displays GUI controls that allow the user to select the nature of the vibration. In the example shown in view 202e, the GUI controls include "Vibrate Continuously," "Vibrate Intermittently," and "Vibrate in Pattern." In one embodiment, the vibration pattern is configurable, as will be described in more detail below.

As shown in view 202f, the activity tracking application 202 also displays GUI controls that allow a user to configure the contact gestures that can be applied to the activity tracking device to either turn the alarm off or transition the alarm into a snooze mode. In the example shown in view 202f, the alarm will be placed into a snooze mode when the activity tracking device detects that a surface of the activity tracking device has received a double tap (two (2) taps). Further, the alarm will be turned off when the activity tracking device detects one of the following: a button press; three (3) taps to a surface of the activity tracking device; or four (4) taps to a surface of the activity tracking device. It will be appreciated that the configuration shown in view 202f is an example and that this configuration can be varied to suit the needs of the user. Once the alarm settings have been configured, as shown in view 202g, the alarm settings are saved and the saved alarm settings 230 can be accessed by the server 220, as described above.

Figure 4:
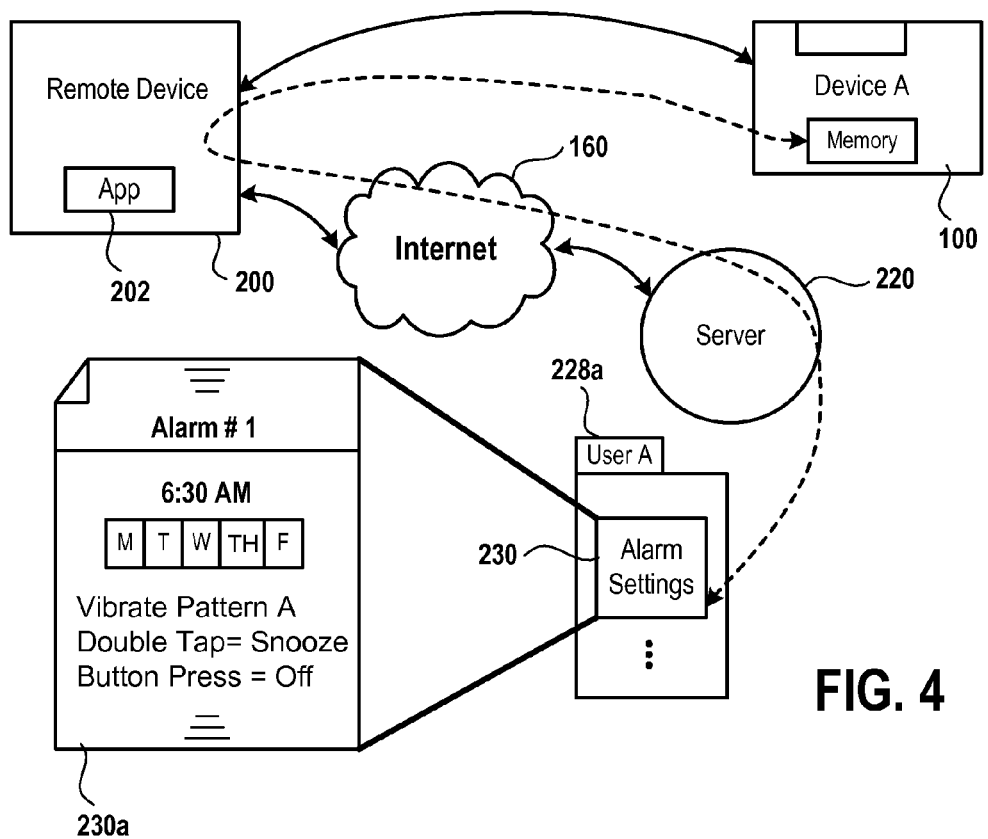
FIG. 4 is a block diagram that illustrates how the alarm settings configured using a remote device, e.g., a smartphone or tablet computing device, are made available to one or more activity tracking devices, in accordance with one embodiment of the present invention.

FIG. 4 is a block diagram that illustrates how the alarm settings configured using a remote device, e.g., a smartphone or tablet computing device, are made available to one or more activity tracking devices, in accordance with one embodiment of the present invention. As shown in FIG. 4, the configured alarm settings 230 for user account 228a for a User A are stored on the server 220. In the example alarm settings 230a shown in the figure, the alarm settings for "Alarm #1" have been set to trigger an alarm at 6:30 am on weekdays (Monday thru Friday). Further, the alarm settings have been configured to 1) trigger a non-audible alarm that uses "Vibrate Pattern A," 2) place the alarm in a snooze mode when a surface of the activity tracking device is detected to receive a "Double Tap," and 3) turn the alarm off when a button of the activity tracking device is pressed. These alarm settings can be configured using activity tracking application 202 of remote device 200, as described above with reference to FIG. 3.

The alarm settings configured using activity tracking application 202 of remote device 200 are saved to a memory of the remote device. When an Internet connection is available to remote device 200, the alarm settings are uploaded to server 220 via the Internet 160. As described above, the server 220 stores user profiles in storage 226. The alarm settings for a particular user are stored in that user's account (see, e.g., alarm settings 230 in user account 228a for User A). These alarm settings can be transferred to an activity tracking device 100 in several ways, as described below.

Each time the alarm settings are configured using the activity tracking application 202 of a remote device 200, the alarm settings are stored to the server 220. It is possible for a user to configure the alarm settings using multiple remote devices 200. As such, it is also possible that the alarm settings stored on a given remote device 200 might not have the most recent configuration because, e.g., the user changed the configuration of the alarm settings using a different remote device. To make sure that each remote device 200 of a user has the current alarm settings, the activity tracking application 202 on each remote device periodically synchronizes the configuration of alarm settings stored in the memory of the remote device with the configuration of the alarm settings stored on the server 220.

The alarm settings stored in the memory of a remote device 200 can be transferred to an activity tracking device 100 over a Bluetooth connection, as described above. In one embodiment, the Bluetooth connection is a low energy Bluetooth connection (e.g., Bluetooth LE, BLE, or Bluetooth Smart). Whenever an activity tracking device 100, e.g., Device A shown in FIG. 4, comes within a predefined proximity distance of a remote device 200 having an activity tracking application 202, the current alarm settings stored in the memory of the remote device are communicated to the memory of the activity tracking device over the Bluetooth connection. As a result of the synchronization process described above, the current alarm settings stored in the memory of a remote device are typically the same as the alarm settings stored on the server 220. It is possible, however, that a user could change the configuration of the alarm settings on a remote device 200 without uploading the new alarm settings to the server 220. For example, the remote device 200 might not have access to a functioning Internet connection. In this scenario, it is still possible to transfer the newly configured alarm settings from the remote device 200 to an activity tracking device 100 over the Bluetooth connection because the activity tracking application 202 stores the newly configured alarm settings to a memory of the remote device.

Figure 5:
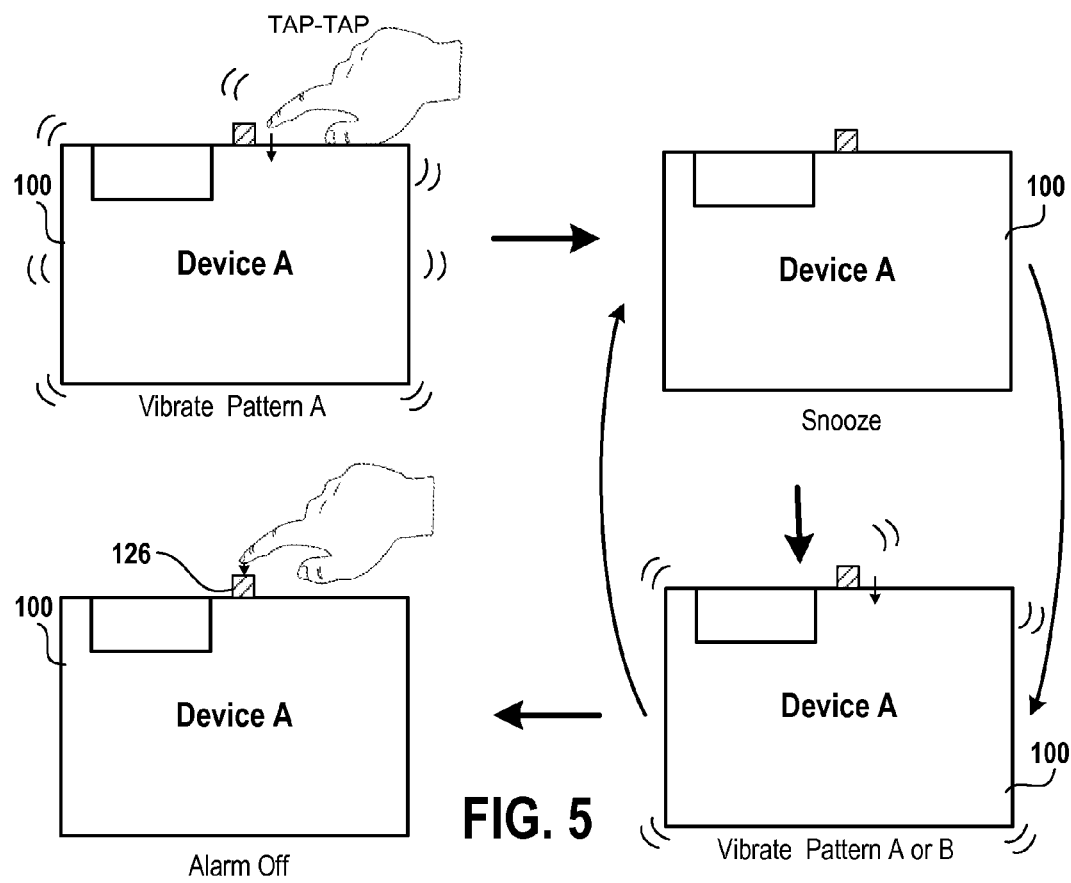
FIG. 5 is a block diagram that illustrates how the alarm of an activity tracking device can be transitioned into a snooze mode or turned off, in accordance with one embodiment of the present invention.

FIG. 5 is a block diagram that illustrates how the alarm of an activity tracking device can be transitioned into a snooze mode or turned off, in accordance with one embodiment of the present invention. In the example shown in FIG. 5, the alarm of activity tracking device 100 produces a vibration in the form of a vibration pattern referred to as "Vibrate Pattern A." When activity tracking device 100 detects that a surface of the device has received a double tap, the alarm is transitioned into a snooze mode and vibration is suspended. After a predefined snooze period, e.g., 2 minutes, 5 minutes, etc., elapses, the alarm is triggered again. In one embodiment, the alarm again produces a vibration in the form of "Vibrate Pattern A." In another embodiment, the alarm produces a vibration in the form of a different vibration pattern referred to as "Vibrate Pattern B." In the event the activity tracking device 100 detects that a surface of the device has received a double tap, the alarm will again be placed in a snooze mode. Once again, the alarm will be triggered after the predefined snooze period elapses, and the process of transitioning the alarm into a snooze mode can be repeated until the alarm is turned off. As shown in FIG. 5, the alarm can be turned off by pressing button 126 of activity tracking device 100.

Figure 6:
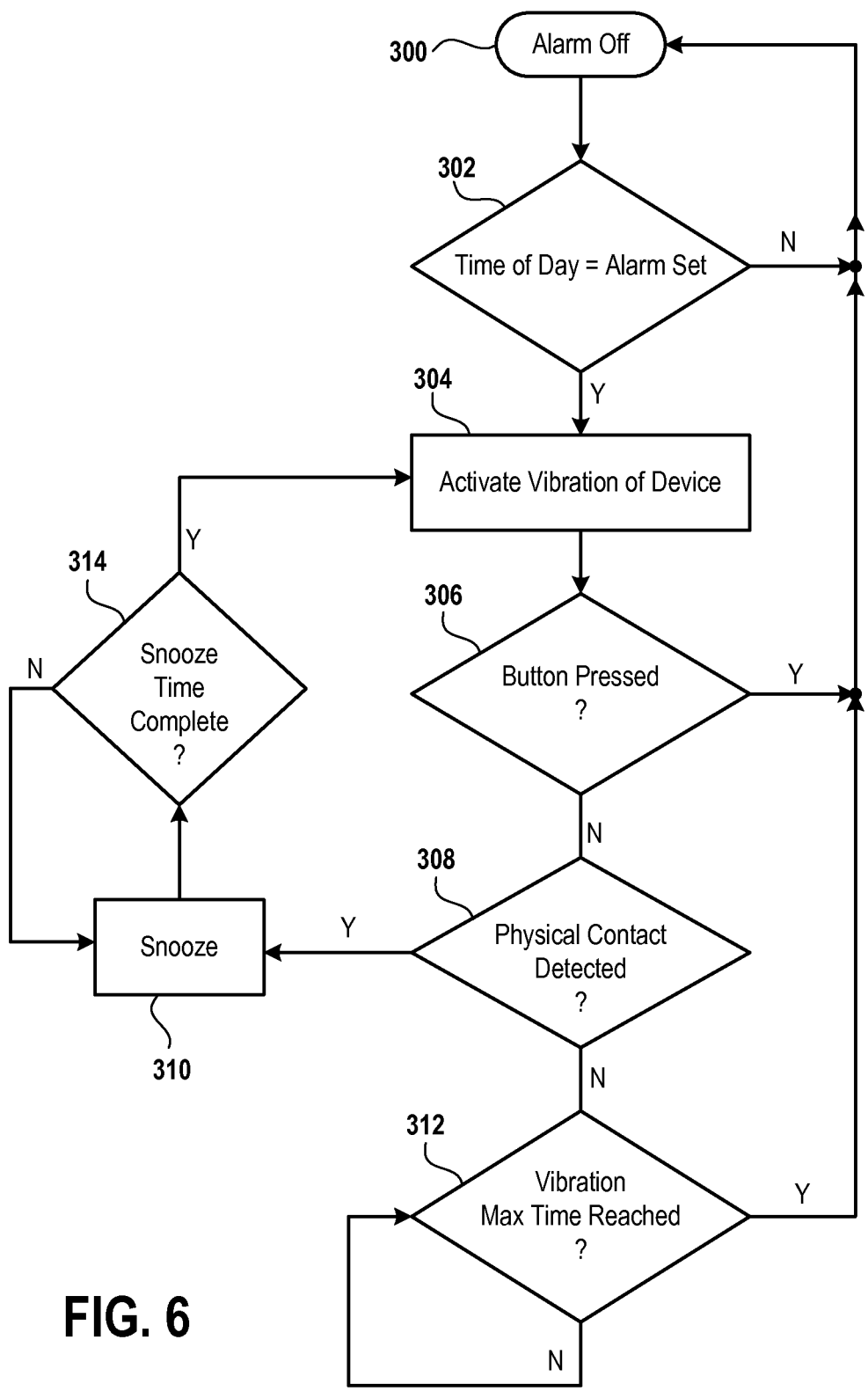
FIG. 6 is a flowchart diagram that shows the method operations performed in implementing an alarm in an activity tracking device, in accordance with one embodiment of the present invention.

FIG. 6 is a flowchart diagram that shows the method operations performed in implementing an alarm in an activity tracking device, in accordance with one embodiment of the present invention. The method begins in operation 300 in which the alarm is maintained in the "off" state. In operation 302, a determination is made as to whether the current time of day is the same as the time at which an alarm is set. If it is determined that an alarm is not set for the current time of day, then the method returns to operation 300 and the alarm continues to be maintained in the "off" mode. If it is determined that an alarm is set for the current time of day, then the method proceeds to operation 304 in which the alarm is triggered. In one embodiment, the alarm is triggered by activating vibration of the activity tracking device. As described above, the vibration may be implemented by a motor that causes vibration of the housing of the activity tracking device.

Once the alarm has been triggered, a determination is made in operation 306 as to whether a button of the activity tracking device has been pressed. If it is determined that a button of the activity tracking device has been pressed, then the alarm is turned off and the method returns to operation 300 in which the alarm is maintained in the "off" state. If it is determined that a button of the activity tracking device has not been pressed, then the method proceeds to operation 308. In operation 308, a determination is made as to whether the activity tracking device has detected physical contact with a surface thereof. In one embodiment, it is determined whether the activity tracking device has detected that a surface thereof has received a contact gesture in the form of a double tap (two (2) taps). It should be appreciated, however, that other predefined numbers of contact gestures can be detected, e.g., three (3) taps or four (4) taps. If it is determined that the activity tracking device has detected a double tap on a surface thereof, then the method proceeds to operation 310. On the other hand, if it is determined that the activity device has not detected any physical contact with a surface thereof, then the method proceeds to operation 312.

In operation 310, in response to the detected double tap on a surface of the activity tracking device, the alarm is transitioned into a snooze mode and vibration is suspended. The method then proceeds to operation 314 in which a determination is made as to whether the snooze period has elapsed. In one embodiment, the snooze period is preset by the system and lasts for a predefined period of time, e.g., 2 minutes, 3 minutes, 5 minutes, etc. In another embodiment, the snooze period is set by a user and lasts for the period of time selected by the user, e.g., 5 minutes, 10 minutes, 15 minutes, etc. If it is determined in operation 314 that the snooze period has not yet elapsed, then the method returns to operation 310 and the alarm remains in snooze mode. On the other hand, if it is determined that the snooze period has elapsed, then the method returns to operation 304 and the alarm is triggered again.

As noted above, when it is determined in operation 308 that the activity device has not detected any physical contact with a surface thereof, the method proceeds to operation 312. In operation 312, a determination is made as to whether the threshold vibration time, which is the maximum allowable vibration time, has been reached. In one embodiment, the maximum allowable vibration time is set by the system and lasts for a predefined period of time, e.g., 5 minutes, 10 minutes, 15 minutes, etc. The alarm will continue to vibrate until it is determined that the maximum allowable vibration time has been reached. Once it is determined that the maximum allowable vibration time has been reached, the alarm is turned off and the method returns to operation 300 in which the alarm is maintained in the "off" mode.

Figure 7:
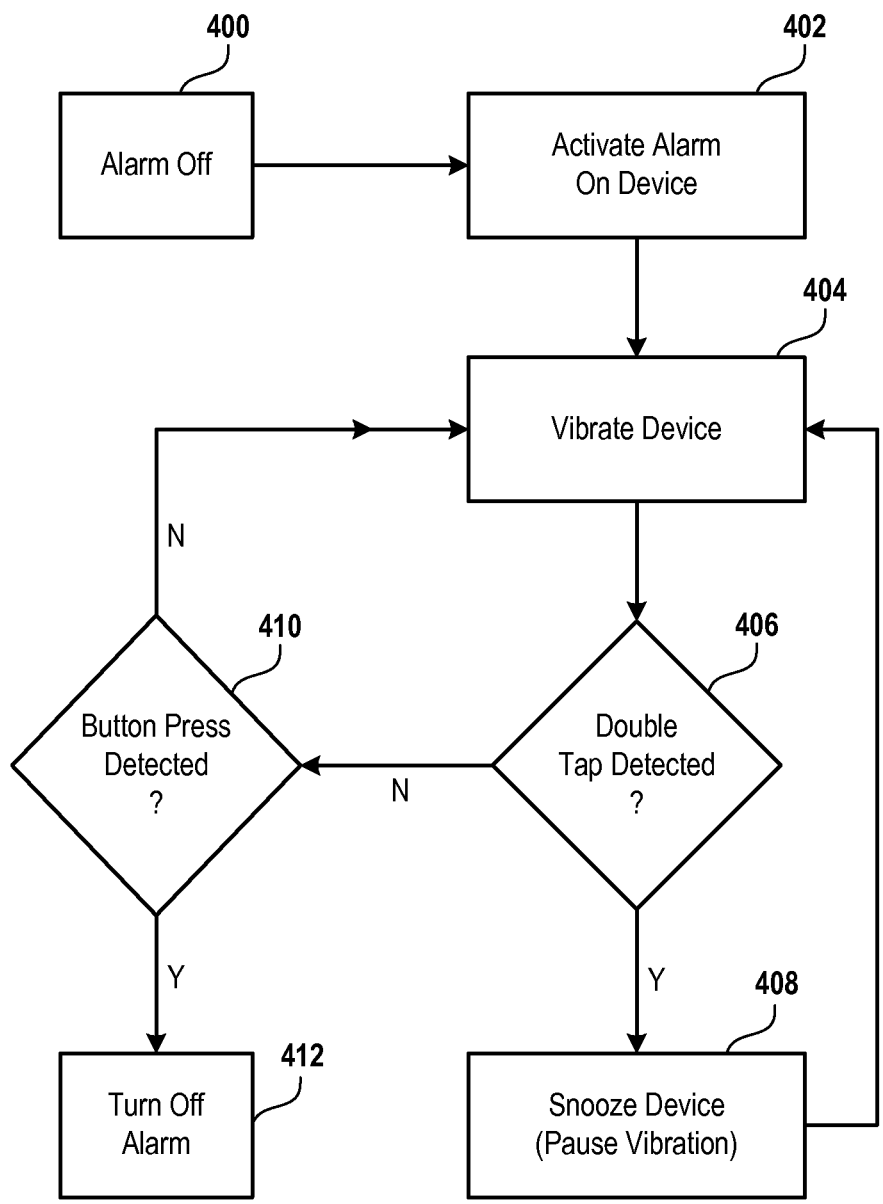
FIG. 7 is a flowchart diagram that shows the method operations performed in implementing an alarm in an activity tracking device, in accordance with another embodiment of the present invention.

FIG. 7 is a flowchart diagram that shows the method operations performed in implementing an alarm in an activity tracking device, in accordance with another embodiment of the present invention. The method begins in operation 400 in which the alarm is maintained in the "off" state. In operation 402, an alarm is activated on an activity tracking device. In response to the alarm being activated, in operation 404, the activity tracking device is vibrated. In one embodiment, the activity tracking device is continuously vibrated. In another embodiment, the activity tracking device is intermittently vibrated. In still another embodiment, the activity tracking device is vibrated in accordance with one or more vibration patterns. Once the alarm is activated, the method proceeds to operation 406 in which a determination is made as to whether the activity tracking device has detected a double tap on a surface thereof. If it is determined that a double tap has been detected, then the method proceeds to operation 408. On the other hand, if it is determined that a double tap has not been detected, then the operation proceeds to operation 410.

In operation 408, in response to the detected double tap, the alarm of the activity tracking device is transitioned into a snooze mode. In this snooze mode, the vibration of the activity tracking device is paused or suspended. When a predefined snooze period elapses, the method returns to operation 404 in which the activity tracking device is vibrated.

As noted above, when no double tap is detected in operation 406, the method proceeds to operation 410. In operation 410, a determination is made as to whether the activity tracking device has detected that a button of the device has been pressed. If it is determined that a button press has been detected, then the method proceeds to operation 412 in which the alarm is turned off. On the other hand, if no button press is detected, then the activity tracking device continues to vibrate and the method returns to operation 404 for further processing.

In the method illustrated in FIG. 7, the alarm is transitioned into a snooze mode when a double tap is detected, and the alarm is turned off when a button press is detected. It should be appreciated that the functionality of the double tap and the button press can be varied from that shown in FIG. 7. For example, the alarm could be placed in a snooze mode when a button press is detected, and the alarm could be turned off when a double tap is detected.

It should be further appreciated that, in some instances, it might not be convenient to press a button of the activity tracking device to turn an alarm off (or to place the alarm in a snooze mode). For example, a user could be engaged in an activity, e.g., running, climbing stairs, etc., and might not want to stop the activity to turn off the alarm. To address such instances, the alarm can be configured to turn off automatically based on activity detected by the activity tracking device. In one embodiment, when the alarm goes off, the activity tracking device monitors the user's current activity level. When the activity tracking device detects that the user has taken a predefined number of steps, e.g., 40 steps, 50 steps, 60 steps, etc., since the alarm went off, the alarm is turned off automatically without requiring any physical contact with the device on the part of the user. In another embodiment, when the alarm goes off, the activity tracking device not only monitor's the user's current activity level but also takes into account the user's activity level during a predefined period of time before the alarm went off, e.g., 1 minute, 2 minutes, etc. For example, if a runner had taken 90 steps in the minute before the alarm went off and the alarm was configured to turn after the user had taken 100 steps, then the alarm would be automatically turned off after the activity tracking device detected that the user had taken an additional 10 steps (for a total of 100 steps) since the alarm went off.

Figure 8:
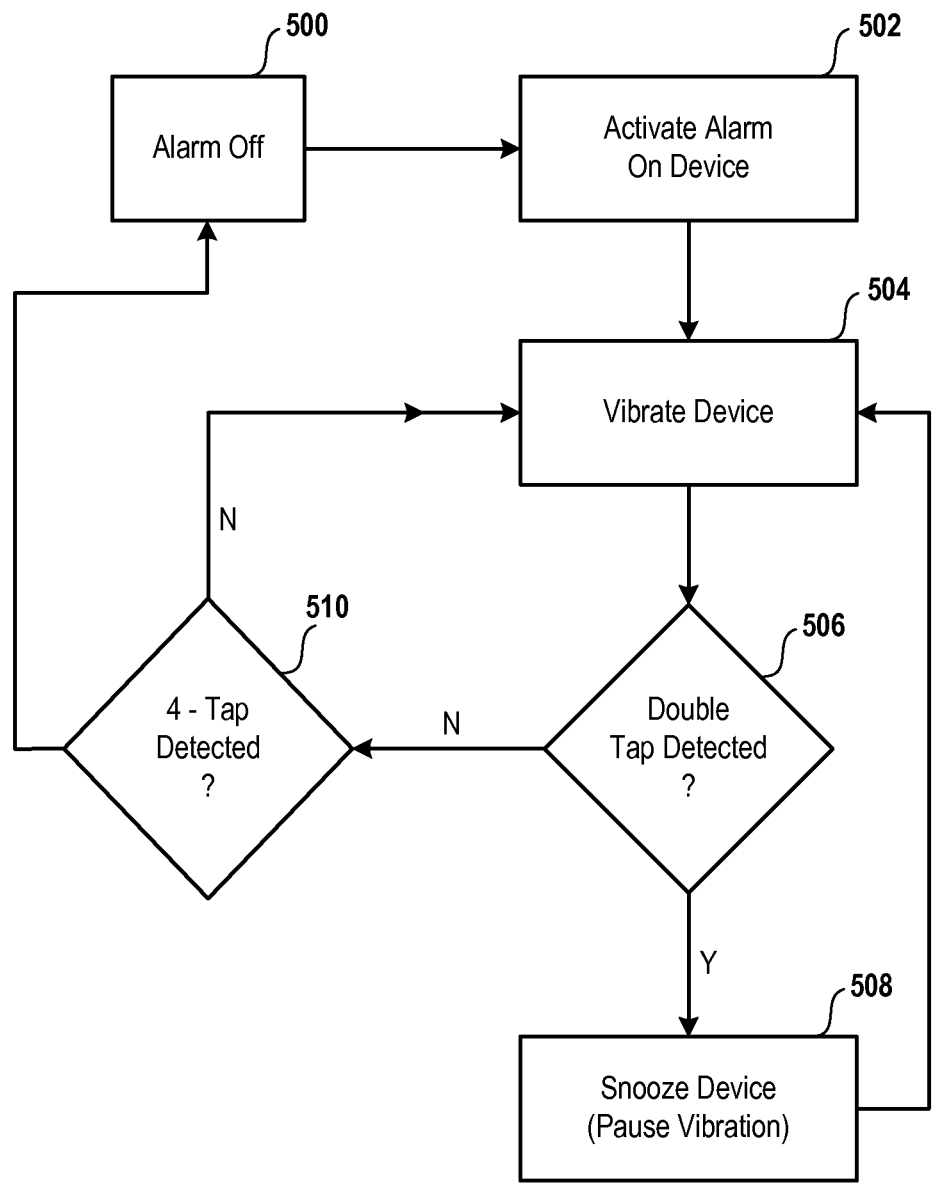
FIG. 8 is a flowchart diagram that shows the method operations performed in implementing an alarm in an activity tracking device, in accordance with yet another embodiment of the present invention.

FIG. 8 is a flowchart diagram that shows the method operations performed in implementing an alarm in an activity tracking device, in accordance with yet another embodiment of the present invention. The method shown in FIG. 8 does not require the use of a button press to turn the alarm off. Consequently, this method can be implemented in activity tracking devices that do not include a button. The method begins in operation 500 in which the alarm is maintained in the "off" state or the "off" mode. In operation

502, an alarm is activated on an activity tracking device. In response to the alarm being activated, in operation 504, the activity tracking device is vibrated. Once the alarm is activated, the method proceeds to operation 506 in which a determination is made as to whether the activity tracking device has detected a double tap on a surface thereof. If it is determined that a double tap has been detected, then the method proceeds to operation 508. On the other hand, if it is determined that a double tap has not been detected, then the operation proceeds to operation 510.

In operation 508, in response to the detected double tap, the alarm of the activity tracking device is transitioned into a snooze mode. In this snooze mode, the vibration of the activity tracking device is paused or suspended. When a predefined snooze period elapses, the method returns to operation 504 in which the activity tracking device is vibrated.

As noted above, when no double tap is detected in operation 506, the method proceeds to operation 510. In operation 510, a determination is made as to whether the activity tracking device has detected four (4) taps ("a four tap") on a surface of the activity tracking device. If it is determined that a four tap has been detected, then the alarm is turned off and the method returns to operation 500 in which the alarm is maintained in the "off" state. On the other hand, if no four tap is detected, then the activity tracking device continues to vibrate and the method returns to operation 504 for further processing.

Figure 9:
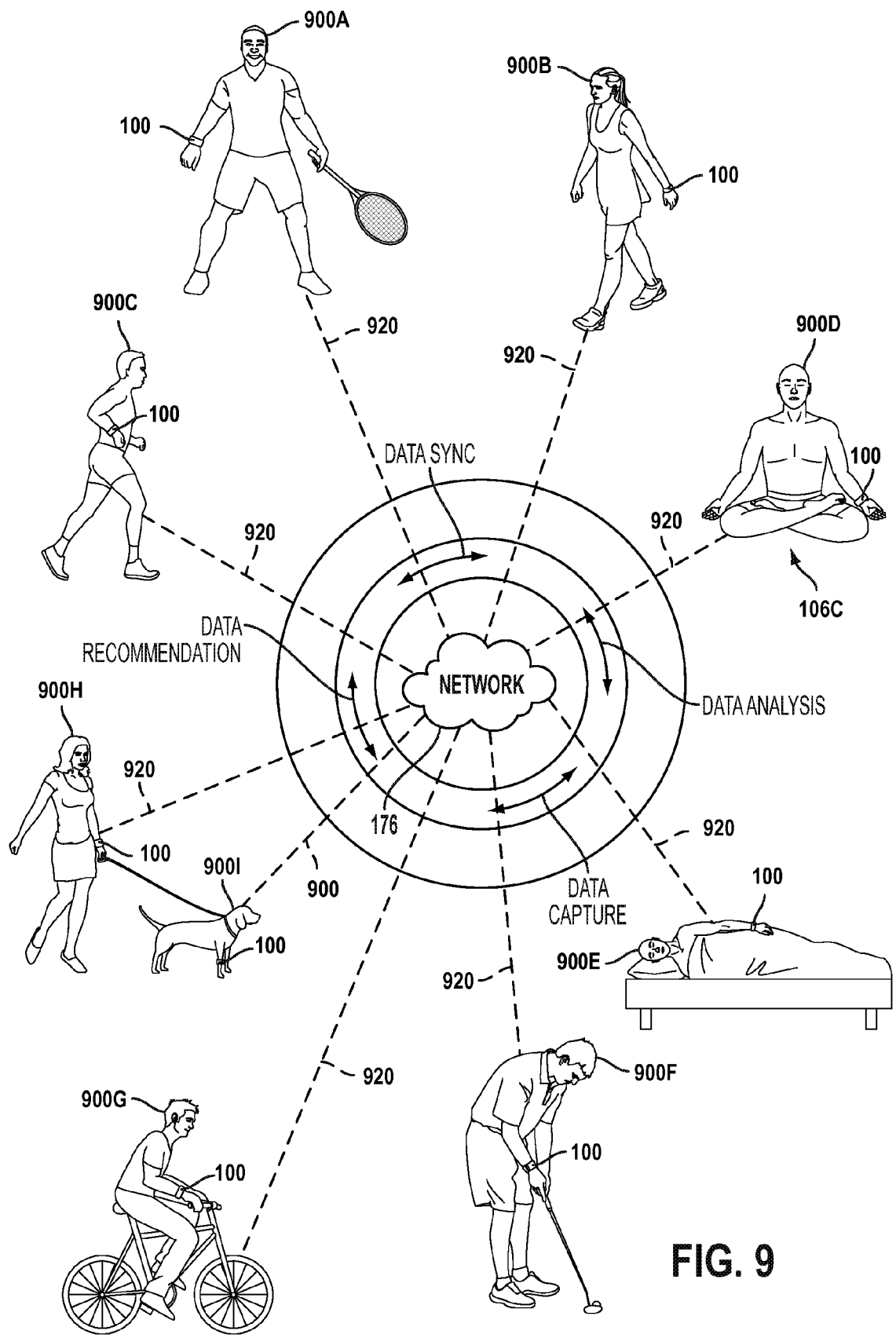
FIG. 9 illustrates an example where various types of activities of users can be captured by activity tracking devices, in accordance with one embodiment of the present invention.

FIG. 9 illustrates an example where various types of activities of users 900A-900I can be captured by activity tracking devices 100, in accordance with one embodiment of the present invention. As shown, the various types of activities can generate different types of data that can be captured by the activity tracking device 100. The data, which can be represented as motion data (or processed motion data) can be transferred 920 to a network 176 for processing and saving by a server, as described above. In one embodiment, the activity tracking device 100 can communicate to a device using a wireless connection, and the device is capable of communicating and synchronizing the captured data with an application running on the server. In one embodiment, an application running on a local device, such as a smartphone or tablet or smartwatch can capture or receive data from the activity tracking device 100 and represent the tracked motion data in a number of metrics.

In one embodiment, the device collects one or more types of physiological and/or environmental data from embedded sensors and/or external devices and communicates or relays such metric information to other devices, including devices capable of serving as Internet-accessible data sources, thus permitting the collected data to be viewed, for example, using a web browser or network-based application. For example, while the user is wearing an activity tracking device, the device may calculate and store the user's step count using one or more sensors. The device then transmits data representative of the user's step count to an account on a web service, computer, mobile phone, or health station where the data may be stored, processed, and visualized by the user. Indeed, the device may measure or calculate a plurality of other physiological metrics in addition to, or in place of, the user's step count.

Some physiological metrics include, but are not limited to, energy expenditure (for example, calorie burn), floors climbed and/or descended, heart rate, heart rate variability, heart rate recovery, location and/or heading (for example, through GPS), elevation, ambulatory speed and/or distance traveled, swimming lap count, bicycle distance and/or speed, blood pressure, blood glucose, skin conduction, skin and/or body temperature, electromyography, electroencephalography, weight, body fat, caloric intake, nutritional intake from food, medication intake, sleep periods (i.e., clock time), sleep phases, sleep quality and/or duration, pH levels, hydration levels, and respiration rate. The device may also measure or calculate metrics related to the environment around the user such as barometric pressure, weather conditions (for example, temperature, humidity, pollen count, air quality, rain/snow conditions, wind speed), light exposure (for example, ambient light, UV light exposure, time and/or duration spent in darkness), noise exposure, radiation exposure, and magnetic field.

Still further, other metrics can include, without limitation, calories burned by a user, weight gained by a user, weight lost by a user, stairs ascended, e.g., climbed, etc., by a user, stairs descended by a user, steps taken by a user during walking or running, a number of rotations of a bicycle pedal rotated by a user, sedentary activity data, driving a vehicle, a number of golf swings taken by a user, a number of forehands of a sport played by a user, a number of backhands of a sport played by a user, or a combination thereof. In some embodiments, sedentary activity data is referred to herein as inactive activity data or as passive activity data. In some embodiments, when a user is not sedentary and is not sleeping, the user is active. In some embodiments, a user may stand on a monitoring device that determines a physiological parameter of the user. For example, a user stands on a scale that measures a weight, a body fat percentage, a biomass index, or a combination thereof, of the user.

Furthermore, the device or the system collating the data streams may calculate metrics derived from this data. For example, the device or system may calculate the user's stress and/or relaxation levels through a combination of heart rate variability, skin conduction, noise pollution, and sleep quality. In another example, the device or system may determine the efficacy of a medical intervention (for example, medication) through the combination of medication intake, sleep and/or activity data. In yet another example, the device or system may determine the efficacy of an allergy medication through the combination of pollen data, medication intake, sleep and/or activity data. These examples are provided for illustration only and are not intended to be limiting or exhaustive.

This information can be associated with the user's account, which can be managed by an activity management application on the server. The activity management application can provide access to the users account and data saved thereon. The activity manager application running on the server can be in the form of a web application. The web application can provide access to a number of websites screens and pages that illustrate information regarding the metrics in various formats. This information can be viewed by the user, and synchronized with a computing device of the user, such as a smartphone.

In one embodiment, the data captured by the activity tracking device 100 is received by the computing device, and the data is synchronized with the activity measured application on the server. In this example, data viewable on the computing device (e.g. smartphone) using an activity tracking application (app) can be synchronized with the data present on the server, and associated with the user's account. In this way, information entered into the activity tracking application on the computing device can be synchronized with application illustrated in the various screens of the activity management application provided by the server on the website.

The user can therefore access the data associated with the user account using any device having access to the Internet. Data received by the network 176 can then be synchronized with the user's various devices, and analytics on the server can provide data analysis to provide recommendations for additional activity, and or improvements in physical health. The process therefore continues where data is captured, analyzed, synchronized, and recommendations are produced. In some embodiments, the captured data can be itemized and partitioned based on the type of activity being performed, and such information can be provided to the user on the website via graphical user interfaces, or by way of the application executed on the users smart phone (by way of graphical user interfaces).

In an embodiment, the sensor or sensors of a device 100 can determine or capture data to determine an amount of movement of the monitoring device over a period of time. The sensors can include, for example, an accelerometer, a magnetometer, a gyroscope, or combinations thereof. Broadly speaking, these sensors are inertial sensors, which capture some movement data, in response to the device 100 being moved. The amount of movement (e.g., motion sensed) may occur when the user is performing an activity of climbing stairs over the time period, walking, running, etc. The monitoring device may be worn on a wrist, carried by a user, worn on clothing (using a clip, or placed in a pocket), attached to a leg or foot, attached to the user's chest, waist, or integrated in an article of clothing such as a shirt, hat, pants, blouse, glasses, and the like. These examples are not limiting to all the possible ways the sensors of the device can be associated with a user or thing being monitored.

In other embodiments, a biological sensor can determine any number of physiological characteristics of a user. As another example, the biological sensor may determine heart rate, a hydration level, body fat, bone density, fingerprint data, sweat rate, and/or a bioimpedance of the user. Examples of the biological sensors include, without limitation, a biometric sensor, a physiological parameter sensor, a pedometer, or a combination thereof.

In some embodiments, data associated with the user's activity can be monitored by the applications on the server and the user's device, and activity associated with the user's friends, acquaintances, or social network peers can also be shared, based on the user's authorization. This provides for the ability for friends to compete regarding their fitness, achieve goals, receive badges for achieving goals, get reminders for achieving such goals, rewards or discounts for achieving certain goals, etc.

As noted, an activity tracking device 100 can communicate with a computing device (e.g., a smartphone, a tablet computer, a desktop computer, or computer device having wireless communication access and/or access to the Internet). The computing device, in turn, can communicate over a network, such as the Internet or an Intranet to provide data synchronization. The network may be a wide area network, a local area network, or a combination thereof. The network may be coupled to one or more servers, one or more virtual machines, or a combination thereof. A server, a virtual machine, a controller of a monitoring device, or a controller of a computing device is sometimes referred to herein as a computing resource. Examples of a controller include a processor and a memory device.

In one embodiment, the processor may be a general purpose processor. In another embodiment, the processor can be a customized processor configured to run specific algorithms or operations. Such processors can include digital signal processors (DSPs), which are designed to execute or interact with specific chips, signals, wires, and perform certain algorithms, processes, state diagrams, feedback, detection, execution, or the like. In some embodiments, a processor can include or be interfaced with an application specific integrated circuit (ASIC), a programmable logic device (PLD), a central processing unit (CPU), or a combination thereof, etc.

In some embodiments, one or more chips, modules, devices, or logic can be defined to execute instructions or logic, which collectively can be viewed or characterized to be a processor. Therefore, it should be understood that a processor does not necessarily have to be one single chip or module, but can be defined from a collection of electronic or connecting components, logic, firmware, code, and combinations thereof.

Examples of a memory device include a random access memory (RAM) and a read-only memory (ROM). A memory device may be a Flash memory, a redundant array of disks (RAID), a hard disk, or a combination thereof.

Embodiments described in the present disclosure may be practiced with various computer system configurations including hand-held devices, microprocessor systems, microprocessor-based or programmable consumer electronics, minicomputers, mainframe computers and the like. Several embodiments described in the present disclosure can also be practiced in distributed computing environments where tasks are performed by remote processing devices that are linked through a wire-based or wireless network.

With the above embodiments in mind, it should be understood that a number of embodiments described in the present disclosure can employ various computer-implemented operations involving data stored in computer systems. These operations are those requiring physical manipulation of physical quantities. Any of the operations described herein that form part of various embodiments described in the present disclosure are useful machine operations. Several embodiments described in the present disclosure also relate to a device or an apparatus for performing these operations. The apparatus can be specially constructed for a purpose, or the apparatus can be a computer selectively activated or configured by a computer program stored in the computer. In particular, various machines can be used with computer programs written in accordance with the teachings herein, or it may be more convenient to construct a more specialized apparatus to perform the required operations.

Various embodiments described in the present disclosure can also be embodied as computer-readable code on a non-transitory computer-readable medium. The computer-readable medium is any data storage device that can store data, which can thereafter be read by a computer system. Examples of the computer-readable medium include hard drives, network attached storage (NAS), ROM, RAM, compact disc-ROMs (CD-ROMs), CD-recordables (CD-Rs), CD-rewritables (RWs), magnetic tapes and other optical and non-optical data storage devices. The computer-readable medium can include computer-readable tangible medium distributed over a network-coupled computer system so that the computer-readable code is stored and executed in a distributed fashion.

Although the method operations were described in a specific order, it should be understood that other housekeeping operations may be performed in between operations, or operations may be performed in an order other than that shown, or operations may be adjusted so that they occur at slightly different times, or may be distributed in a system which allows the occurrence of the processing operations at various intervals associated with the processing.

Although the foregoing embodiments have been described in some detail for purposes of clarity of understanding, it will be apparent that certain changes and modifications can be practiced within the scope of the appended claims. Accordingly, the present embodiments are to be considered as illustrative and not restrictive, and the various embodiments described in the present disclosure are not to be limited to the details given herein, but may be modified within the scope and equivalents of the appended claims.

What is claimed is:

1. A method, comprising:
receiving an alarm setting that defines a time of day for triggering an alarm on a device for tracking activity data of a user;
activating the alarm upon reaching the time of day defined by the alarm setting, the alarm producing a vibration of the device;
determining a level of activity of the user detected by the device for tracking activity data of the user when the alarm is activated; and
automatically deactivating the alarm if the level of activity qualifies for deactivating the alarm, the deactivating causing the vibration of the device to be suspended, wherein the method is executed by a processor.

2. The method of claim 1, wherein the vibration being suspended transitions the alarm into one of a snooze mode or an off mode.

3. The method of claim 2, wherein the snooze mode continues for a predetermined period of time before reactivating the alarm, wherein the method further includes transitioning the alarm into the snooze mode one or more times until entering the off mode or processing the vibration for a threshold period of time.

4. The method of claim 2, wherein the vibration being suspended transitions the alarm into the off mode.

5. The method of claim 1, wherein the level of activity that qualifies for deactivating the alarm is a predetermined number of steps.

6. The method of claim 5, wherein the predetermined number of steps is detected after the alarm is activated.

7. The method of claim 5, wherein the predetermined number of steps is detected during a period of time that includes a time period before the alarm is activated.

8. The method of claim 1, wherein the alarm setting is received wirelessly from a computing device.

9. The method of claim 8, wherein the alarm setting is transferred from a server to the computing device over the Internet and from the computing device to the device via a wireless Bluetooth connection.

10. A device configured for capture of activity data for a user, comprising:
a housing;
a motor for causing vibration of the housing of the device;
a sensor disposed in the housing to track activity data of the user;
a memory for storing an alarm setting that defines a time of day for triggering an alarm on the device; and
a processor for activating the alarm upon reaching the time of day defined by the alarm setting, the alarm causing the motor to produce the vibration of the housing, the sensor being interfaced with the processor and configured to detect a current level of activity of the user, and the processor being configured to automatically deactivate the alarm if the current level of activity qualifies for deactivating the alarm, the deactivating causing the vibration of the device to be suspended.

11. The device of claim 10, wherein the housing is part of a wearable wrist attachable structure, or an attachable structure that can be carried or worn by the user.

12. The device of claim 10, wherein the wearable wrist attachable structure is defined at least partially from a plastic material.

13. The device of claim 10, wherein the housing further includes wireless communication logic.

14. The device of claim 13, wherein the wireless communication logic includes one of WiFi processing logic, or Bluetooth (BT) processing logic, or radio processing logic.

15. The device of claim 13, wherein the wireless communication logic is configured to pair with a portable computing device or a computer, and the portable computing device or the computer is configured for communication over the Internet with a server, the server having processing instructions for configuring the alarm setting.

16. The device of claim 10, wherein the vibration being suspended transitions the alarm into one of a snooze mode or an off mode.

17. The device of claim 16, wherein the processor configures the snooze mode to continue for a predetermined period of time before reactivating the alarm, and the processor transitions the alarm into the snooze mode one or more times until entering the off mode or processing the vibration for a threshold period of time.

18. One or more non-transitory computer readable media including instructions which, when executed by a processor, cause the processor to:
receive an alarm setting that defines a time of day for triggering an alarm on a device for tracking activity data of a user;
activate the alarm upon reaching the time of day defined by the alarm setting, the alarm producing a vibration of the device;
determine a level of activity of the user detected by the device for tracking activity data of the user when the alarm is activated; and
automatically deactivate the alarm if the level of activity qualifies for deactivating the alarm, the deactivating causing the vibration of the device to be suspended.

19. The one or more non-transitory computer readable media of claim 18, wherein the vibration being suspended transitions the alarm into one of a snooze mode or an off mode.

20. The one or more non-transitory computer readable media of claim 19, wherein the snooze mode continues for a predetermined period of time before reactivating the alarm, wherein the instructions further cause the processor to transition the alarm into the snooze mode one or more times until entering the off mode or processing the vibration for a threshold period of time.

21. The one or more non-transitory computer readable media of claim 18, wherein the vibration being suspended transitions the alarm into the off mode.

22. The one or more non-transitory computer readable media of claim 18, wherein the level of activity that qualifies for deactivating the alarm is a predetermined number of steps.

23. The one or more non-transitory computer readable media of claim 22, wherein the predetermined number of steps is detected after the alarm is activated.

24. The one or more non-transitory computer readable media of claim 22, wherein the predetermined number of steps is detected during a period of time that includes a time period before the alarm is activated.

\* \* \* \* \*